United States Patent
Mercer et al.

(10) Patent No.: US 10,112,017 B2
(45) Date of Patent: Oct. 30, 2018

(54) PEN TYPE DRUG INJECTION DEVICE WITH LOW FRICTION DOSE ENCODER MECHANISM ON THREAD

(71) Applicant: Sanofi-Aventis Deutschland GmbH, Frankfurt am Main (DE)

(72) Inventors: David Richard Mercer, Dorset (GB); George Cave, Warwickshire (GB); Paul Richard Draper, Worcestershire (GB); Samuel Steel, Warwickshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 520 days.

(21) Appl. No.: 14/759,908

(22) PCT Filed: Jan. 13, 2014

(86) PCT No.: PCT/EP2014/050465
§ 371 (c)(1),
(2) Date: Jul. 8, 2015

(87) PCT Pub. No.: WO2014/111338
PCT Pub. Date: Jul. 24, 2014

(65) Prior Publication Data
US 2015/0352289 A1    Dec. 10, 2015

(30) Foreign Application Priority Data
Jan. 15, 2013 (EP) ..................... 13151367

(51) Int. Cl.
*A61M 5/00* (2006.01)
*A61M 5/315* (2006.01)
(Continued)

(52) U.S. Cl.
CPC .... *A61M 5/31568* (2013.01); *A61M 5/31513* (2013.01); *A61M 5/31525* (2013.01);
(Continued)

(58) Field of Classification Search
CPC .......... A61M 5/31525; A61M 5/31535; A61M 5/31566; A61M 5/31568; A61M 5/31513; A61M 5/31528
(Continued)

(56) References Cited

U.S. PATENT DOCUMENTS

| | | |
|---|---|---|
| 533,575 A | 2/1895 | Wilkens |
| 5,226,895 A | 7/1993 | Harris |

(Continued)

FOREIGN PATENT DOCUMENTS

| | | |
|---|---|---|
| CN | 101489607 A | 7/2009 |
| CN | 101557850 A | 10/2009 |

(Continued)

OTHER PUBLICATIONS

English Translation of First Office Action issued in Chinese Patent Application No. 20148004479.4 dated Apr. 28, 2017.
(Continued)

*Primary Examiner* — Edelmira Bosques
(74) *Attorney, Agent, or Firm* — Fish & Richardson P.C.

(57) ABSTRACT

A drug delivery device comprises a body component located concentrically within a sleeve, wherein the body component comprises body component thread features and the sleeve comprises sleeve thread features that engage with the body component thread features such that the body component is caused to rotate within the sleeve as the body component and the sleeve component move axially with respect to one another by force of an engaging face of the sleeve thread features against an engaging face of the body component thread features causing sliding of the engaging face of the sleeve thread features over the engaging face of the body component thread features. One of the body component and the sleeve constitutes a first part and the other of the body component and the sleeve constitutes a second part. A (Continued)

conductive track pattern is formed on the thread features of the first part and plural contacts are formed on the second part such as to contact the conductive track pattern as the body component rotates within the sleeve.

20 Claims, 21 Drawing Sheets

(51) Int. Cl.
  *G01D 5/165* (2006.01)
  *G01F 11/02* (2006.01)
(52) U.S. Cl.
  CPC .... *A61M 5/31528* (2013.01); *A61M 5/31535* (2013.01); *A61M 5/31566* (2013.01); *G01D 5/165* (2013.01); *G01F 11/023* (2013.01); *G01F 11/025* (2013.01); *G01F 11/029* (2013.01); *A61M 5/31551* (2013.01); *A61M 2205/3317* (2013.01)
(58) Field of Classification Search
  USPC ......................................................... 604/211
  See application file for complete search history.

(56) References Cited

U.S. PATENT DOCUMENTS

| | | |
|---|---|---|
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,585,698 B1 * | 7/2003 | Packman ............... A61M 5/24 604/207 |
| 6,899,698 B2 | 5/2005 | Sams |
| 6,936,032 B1 | 8/2005 | Bush, Jr. et al. |
| 7,241,278 B2 | 7/2007 | Moller |
| 8,348,904 B2 | 1/2013 | Petersen |
| 8,708,957 B2 | 4/2014 | Jespersen et al. |
| 9,186,465 B2 | 11/2015 | Jorgensen et al. |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0123829 A1 | 5/2007 | Atterbury et al. |
| 2008/0183139 A1* | 7/2008 | Burren ............... A61M 5/31553 604/211 |
| 2009/0076460 A1 | 3/2009 | Nielsen et al. |
| 2009/0275916 A1 | 11/2009 | Harms et al. |
| 2010/0042054 A1 | 2/2010 | Elahi et al. |
| 2011/0181301 A1 | 7/2011 | Nielsen et al. |
| 2011/0270214 A1 | 11/2011 | Jorgensen et al. |
| 2014/0142511 A1* | 5/2014 | Gilmore ............ A61M 5/31551 604/189 |

FOREIGN PATENT DOCUMENTS

| | | |
|---|---|---|
| CN | 101641127 A | 2/2010 |
| CN | 101909673 A | 12/2010 |
| CN | 102202711 A | 9/2011 |
| EP | 0937471 A2 | 8/1999 |
| EP | 0937476 A2 | 8/1999 |
| WO | 9938554 A1 | 8/1999 |
| WO | 0110484 A1 | 2/2001 |
| WO | 2006120182 A1 | 11/2006 |
| WO | 2013004844 A1 | 1/2013 |

OTHER PUBLICATIONS

English Translation of Abstract of Chinese Patent Application No. 101489607 dated Jul. 28, 2017.

* cited by examiner

First output: 1000001    Second output: 0000011    Third output: 0000110

| | | | |
|---|---|---|---|
| Contact 1 | 1 | 1 | 1 |
| Contact 2 | 0 | 0 | 0 |
| Contact 3 | 0 | 0 | 0 |
| Contact 4 | 0 | 0 | 0 |
| Contact 5 | 0 | 0 | 0 |
| Contact 6 | 0 | 0 | 0 |
| Contact 7 | 1 | 1 | 1 |
| | 1 | 1 | 1 |
| | 0 | 0 | 0 |
| | 0 | 0 | 0 |
| | 0 | 0 | 0 |
| | 0 | 0 | 0 |

*FIG. 19*

First output: 1010100   Second output: 0010001   Third output: 0000101

FIG. 26

PEN TYPE DRUG INJECTION DEVICE WITH LOW FRICTION DOSE ENCODER MECHANISM ON THREAD

CROSS REFERENCE TO RELATED APPLICATIONS

The present application is a U.S. National Phase Application pursuant to 35 U.S.C. § 371 of International Application No. PCT/EP2014/050465 filed Jan. 13, 2014, which claims priority to European Patent Application No. 13151367.3 filed Jan. 15, 2013. The entire disclosure contents of these applications are herewith incorporated by reference into the present application.

FIELD OF INVENTION

The present invention relates to a drug delivery device.

BACKGROUND

Pen type drug delivery devices have application where regular injection by persons without formal medical training occurs. This is increasingly common among patients having diabetes where self-treatment enables such patients to conduct effective management of their diabetes.

For good or perfect glycemic control, the dose of insulin or insulin glargine has to be adjusted for each individual in accordance with a blood glucose level to be achieved. The present invention relates to injectors, for example hand-held injectors, especially pen-type injectors, that is to injectors of the kind that provide for administration by injection of medicinal products from a multidose cartridge. In particular, the present invention relates to such injectors where a user may set the dose.

A user undertaking self-administration of insulin will commonly need to administer between 1 and 80 International Units.

SUMMARY

A first aspect of the invention provides a drug delivery device comprising:

a body component located concentrically within a sleeve, wherein the body component comprises body component thread features and the sleeve comprises sleeve thread features that engage with the body component thread features such that the body component is caused to rotate within the sleeve as the body component and the sleeve component move axially with respect to one another by force of an engaging face of the sleeve thread features against an engaging face of the body component thread features causing sliding of the engaging face of the sleeve thread features over the engaging face of the body component thread features wherein one of the body component and the sleeve constitutes a first part and the other of the body component and the sleeve constitutes a second part, and wherein a conductive track pattern is formed on the thread features of the first part and plural contacts are formed on the second part such as to contact the conductive track pattern as the body component rotates within the sleeve.

Apparatus so constructed can allow determination of the relative position of the sleeve and the body component through detecting the conductive track pattern whilst providing no or relatively little additional resistance to axial movement of the body component relative to the sleeve compared to a corresponding arrangement in which the conductive track and contacts were absent.

The conductive track pattern may comprise:

a continuous portion that extends helically on the first part and that is not in direct contact with the plural contacts formed on the second part as the body component rotates within the sleeve, and a discontinuous portion that extends helically on the first part, that is connected to the continuous portion of the conductive track pattern and that is in direct contact with the plural contacts formed on the second part as the body component rotates within the sleeve.

The continuous portion can allow an electrical circuit to be provided with conductive portions of the discontinuous portion.

The discontinuous portion of the conductive track pattern may be provided on the engaging face of the thread component of the first part and wherein the continuous portion of the conductive track pattern is provided on a non-engaging face of the thread component of the first part. For instance it may be provided on the side face, rather than the top face for the discontinuous part.

First and second conductive track patterns may be formed on the thread features of the first part and plural contacts are formed on the second part such as to contact the first and second conductive track patterns as the body component rotates within the sleeve.

The conductive track pattern may alternatively consist of a single conductive track pattern.

The sleeve thread features may form parts of first and second ones of different start threads and wherein the sleeve thread features and the body component thread features form parts of first and second ones of different start threads.

The thread features of each thread of the first part may include a conductive track pattern and wherein the thread features of each thread of the second part includes respective plural contacts.

The body component may constitute the first part and the sleeve may constitute the second part.

Alternatively, the sleeve may constitute the first part and the body component may constitute the second part.

Each of the plural contacts may be sprung, thereby to provide a preload force between the sleeve thread features and the body component thread features. This can allow all or part of the preload force to be transferred from the thread features to the longitudinal force that is applied between the sleeve and the body component as they move relative to one another.

The drug delivery device may further comprise a processor configured to receive and interpret electrical signals from each of the electrical contacts to determine the position of the cylindrical member relative to the housing.

BRIEF DESCRIPTION OF THE DRAWINGS

Embodiments will now be described, by way of example only, with reference to the accompanying drawings, in which:

FIG. 19 is a schematic diagram illustrating codes used in a third embodiment of the invention;

FIG. 26 is a schematic diagram illustrating a code forming part of a variation of the third embodiment and showing contact locations and outputs from the contacts.

DETAILED DESCRIPTION

Figure 1:
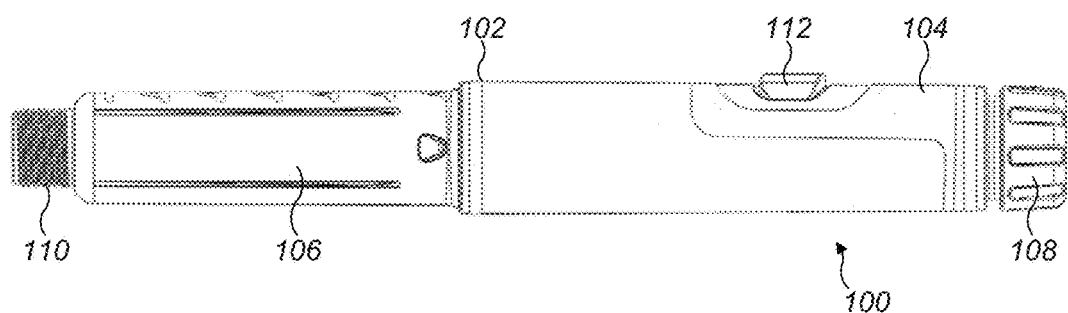
FIG. 1 shows an external view of a drug delivery device 100 suitable for implementing the present invention.

Referring firstly to FIG. 1, an external view of a drug delivery device 100 according to embodiments of the invention is shown. The device 100 shown in FIG. 1 is a pen type injection device, having an elongate cylindrical shape, for setting and delivering a medicament, such as insulin. The device 100 comprises a housing 102 having a first housing part 104 and a second housing part 106. A rotatable dial 108 is located at a first (or proximal) end of the first housing part 104. The rotatable dial 108 has substantially the same outer diameter as the first housing part 104. The second housing part 106 may be detachably connected to the second end of the first housing part 104. The second housing part 106 is configured to have a needle (not shown) or similar drug delivery apparatus attached to it. To achieve this, the second (or distal) end of the second housing part 106 may have a threaded portion 110. The threaded portion 110 may have a smaller diameter than the remainder of the second housing part 106.

A display mount 112 is located on the first housing part 104. A display may be supported on the display mount 112. The display may be an LCD display, a segmented display or any other suitable type of display. The display mount 112 may cover a recess (not shown) in the first housing portion 104. A number of electronic components, described in greater detail with reference to FIG. 2, may be disposed underneath the display mount 112.

The first housing part 104 contains a drug dose setting and delivery mechanism. The second housing part 106 contains a drug cartridge (not shown). The drug contained in the drug cartridge may be a medicament of any kind and may preferably be in a liquid form. The drug delivery mechanism of the first housing part 104 may be configured to engage with the drug cartridge of the second housing part 106 to facilitate expulsion of the drug. The second housing part 106 may be detached from the first housing part 104 in order to insert a drug cartridge or to remove a used cartridge. The first and second housing parts 104, 106 may be connected together in any suitable way, for example with a screw or bayonet type connection. The first and second housing parts 104, 106 may be non-reversibly connected together in such a way that the drug cartridge is permanently contained within the drug delivery device 100. Further the first and second housing parts 104, 106 may form part of a single housing part.

The rotatable dial 108 is configured to be rotated by hand by a user of the drug delivery device 100 in order to set a drug dose to be delivered. The dial 108 may be connected to an internal threading system which causes the dial 108 to be displaced axially from the housing 102 as it is rotated in a first direction. The dial 108 may be rotatable in both directions or only in a first direction. The device 100 is configured, once a drug dose has been set by rotation of the rotatable dial 108, to deliver the set drug dose when a user exerts an axial force at the proximal end of the device. The rotatable dial 108 may support a dose delivery button (416 in FIG. 3) which must be depressed in order to deliver the set drug dose. The display 112 may be configured to display information concerning the drug dose which has been set and/or delivered. The display 112 may further show additional information, such as the actual time, the time of the last usage/injection, a remaining battery capacity, one or more warning signs indicating that a dialled dose has not been fully dispensed, and/or the like.

Figure 2:
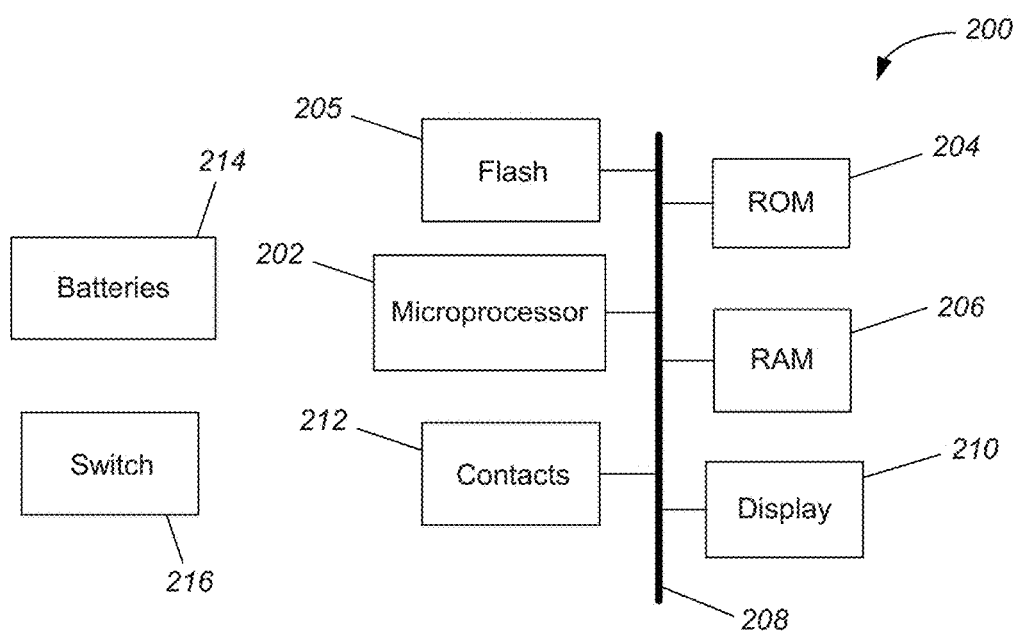
FIG. 2 shows a schematic diagram of some of the electronic components present in the drug delivery device 100 of FIG. 1.

Referring now to FIG. 2, a schematic diagram of electrical circuitry 200 forming part of the drug delivery device 100 is shown. The circuitry 200 comprises a processor 202, a non-volatile memory such as a ROM 204, a writable non-volatile memory such as flash memory 205, a volatile memory such as a RAM 206, a display 210, contacts 212 (described later on as contacts 212a-212i) and a bus 208 connecting each of these components. The circuitry 200 also comprises batteries 214 or some other suitable source of power for providing power to each of the components and a switch 216, described in greater detail below.

The circuitry 200 may be integral with the device 100. Alternatively, the circuitry 200 may be contained within an electronic module that can be attached to the device 100. In addition, the circuitry 200 may comprise additional sensors, such as optical or acoustical sensors. The circuitry 200 may comprise an audible alarm (not shown) which the processor 202 may control to sound an alarm when a dialled dose has not been fully dispensed.

The ROM 204 may be configured to store software and/or firmware. This software/firmware may control operations of the processor 202. The processor 202 utilises RAM 206 to execute the software/firmware stored in the ROM to control operation of the display 210. As such the processor 202 may also comprise a display driver. The processor 202 utilises the flash memory 205 to store determined amounts of dose dialled and/or determined amounts of dose dispensed, as will be described in more detail below.

The batteries 214 may provide power for each of the components including the contacts 212. The supply of electricity to the contacts 212 may be controlled by the processor 202. The processor 202 may receive signals from the contacts 212 and so could determine when the contacts are energised, and is configured to interpret these signals. Information may be provided on the display 210 at suitable times by operation of the software/firmware and the processor 202. This information may include measurements determined from the signals received by the processor 202 from the contacts 212.

A number of contacts 212 may be present in the device 100, as is described below.

Figure 3:
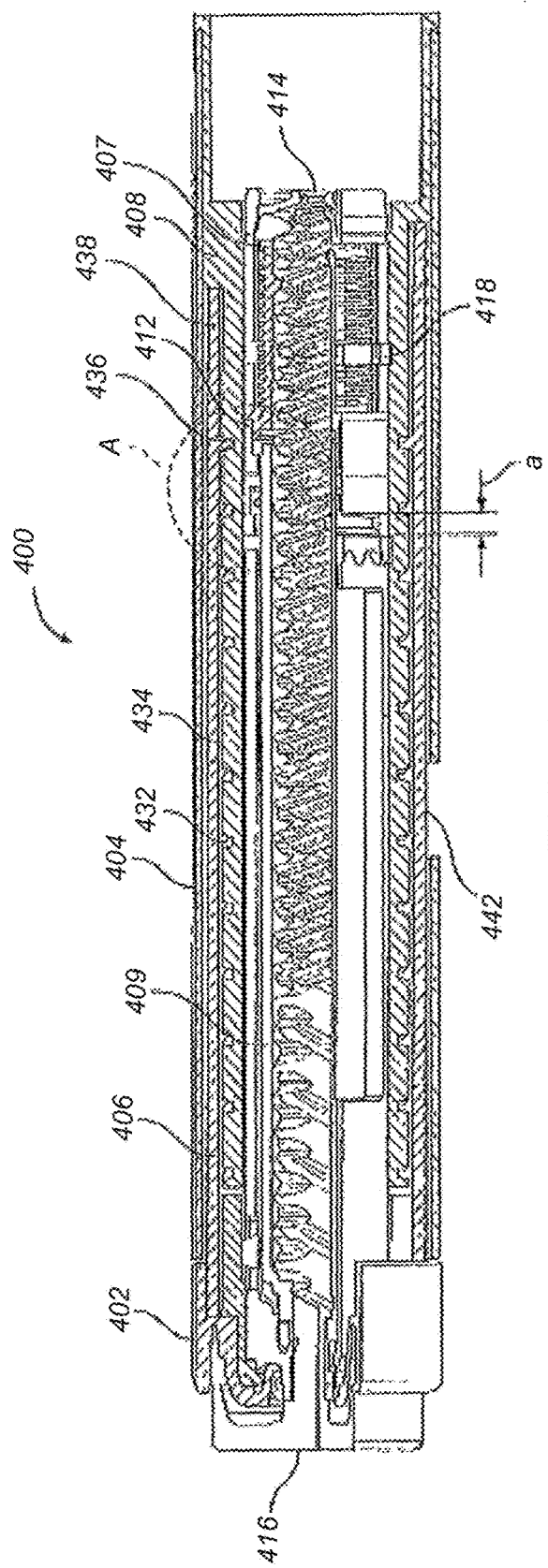
FIG. 3 shows a dose setting mechanism 400 of a drug delivery device 100 suitable for use with the invention.
Figure 4:
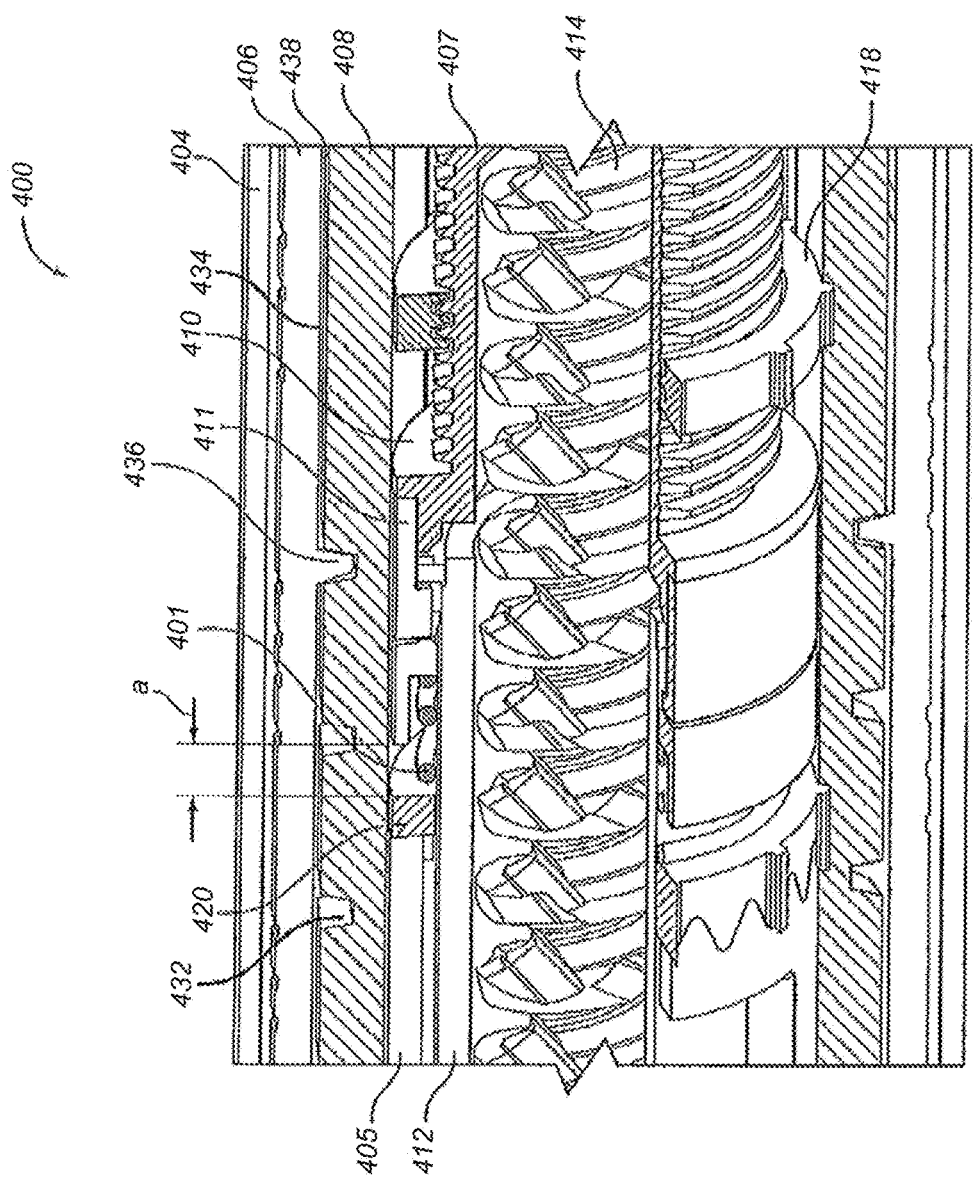
FIG. 4 shows detail of the dose setting mechanism 400 of FIG. 3.
Figure 5:
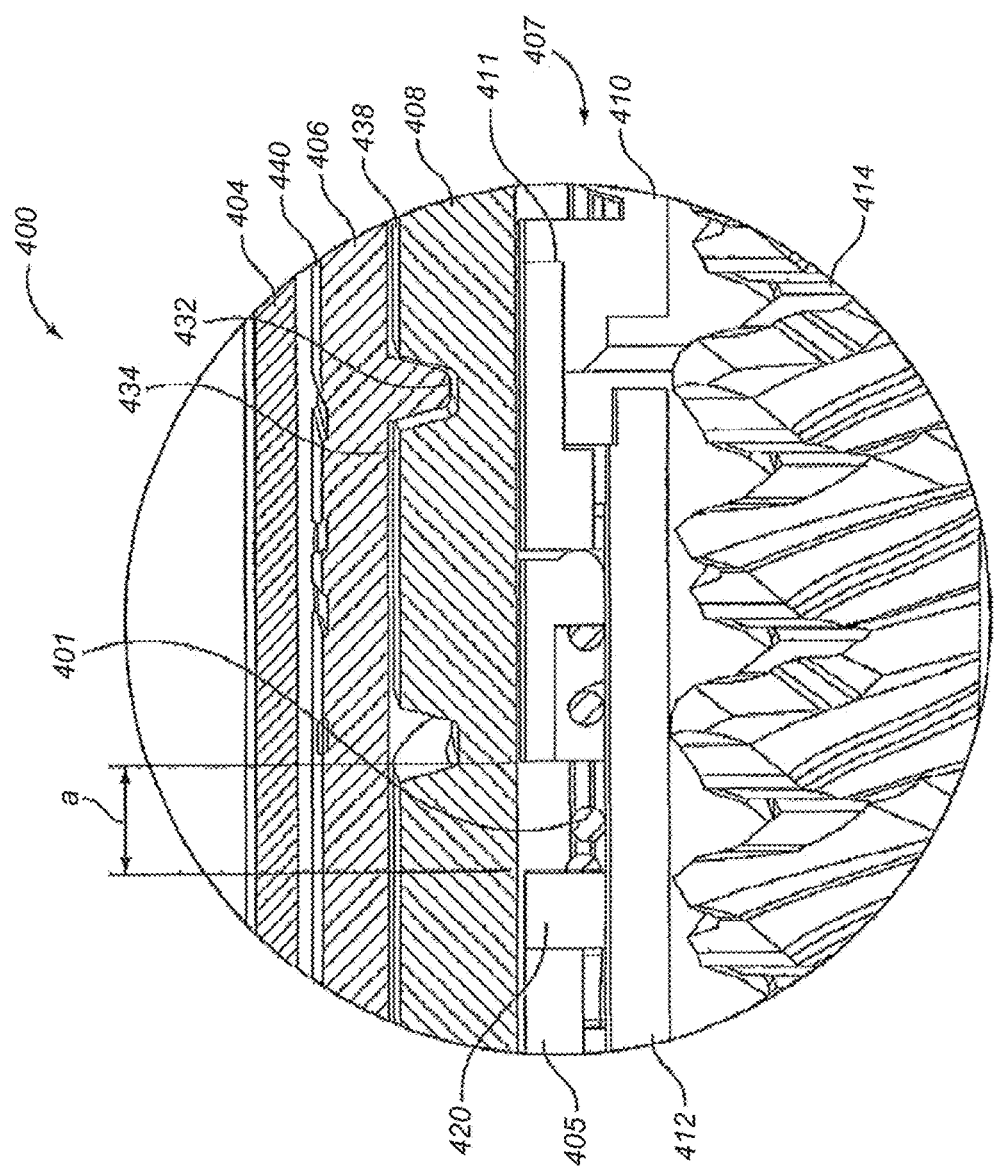
FIG. 5 shows a close up of the region marked 'A' in FIG. 3.

A fuller explanation of the operation of the dose setting and delivery mechanism supported within the first housing part 104 will now be given with reference to FIGS. 3 to 6. FIG. 3 is a cross-sectional view of a dose setting mechanism 400 of a drug delivery device 100. FIG. 4 is a detailed view of a portion of the dose setting mechanism 400. FIG. 5 illustrates a close up view of the region marked 'A' in FIG. 3.

The dose setting mechanism 400 comprises an outer housing 404, an inner housing 408 and a rotatable sleeve 406. The rotatable sleeve 406 is an example of a sleeve. The inner housing 408 is an example of a body component. These components are hollow cylinders arranged concentrically. The rotatable sleeve 406 is disposed between the outer and inner housings 404, 408.

The inner housing 408 comprises a groove 432 provided along an external surface 434 of the inner housing 408. A groove guide 436 provided on an inner surface 438 of the rotatable sleeve 406 is rotatably engaged with this groove 432.

A dose dial grip 402 is located at a proximal end of the outer housing 404. The dose dial grip 402 is disposed about an outer surface of a proximal end of the rotatable sleeve 406. An outer diameter of the dose dial grip 402 preferably corresponds to the outer diameter of the outer housing 404. The dose dial grip 402 is secured to the rotatable sleeve 406 to prevent relative movement between these two components. The dose dial grip 402 is represented in the external view of FIG. 1 by the rotatable dial 108. The dose dial grip 402 supports a dose delivery button dose delivery button 416 which has a sprung bias in a proximal direction and is configured to be depressed into the dose dial grip 402 by a user of the device 100.

A spindle 414 is disposed centrally within the mechanism 400. The spindle 414 is provisioned with at least one helical groove. In the embodiment depicted, the spindle 414 has two opposite handed overlapping groove forms that preferably extend over at least a majority of a length of the spindle. Each groove form is effectively continuous over a number of turns. Each groove of the spindle may engage either a non-continuous helical groove form on a body portion or on a driver. Either or both a non-continuous thread formed on a body and a driver may consist of less than one complete turn of thread. A first thread of the spindle 414 is configured to connect with a portion of the inner housing 408.

The dose setting mechanism 400 also comprises a spring 401, a clutch 405 and a driver 409 having a first driver portion 407 and a second driver portion 412. These driver portions 407, 412 extend about the spindle 414. Both the first and the second driver portions 407, 412 are generally cylindrical. The clutch 405 is disposed about the driver 409. The first driver portion 407 may comprise a first component part 410 and a second component part 411. Alternatively, the first driver portion 407 may be an integral component part.

With the dose setting mechanism 400, as a user dials a dose with the dose dial grip 402, the metal spring 401 is selected to be strong enough to maintain engagement of both clutched couplings: the clutched coupling between the clutch 405 and the rotatable sleeve 406 and clutched coupling between the first driver portion 407 and second driver portion 412. The rotatable sleeve 406 is coupled to the dose dial grip 402 such that when a user rotates the dose dial grip 402, the rotatable sleeve 406 also rotates. As the rotatable sleeve 406 is rotated in a first rotational direction, it moves axially in a proximal direction due to its threaded connection to the inner housing 408.

This threaded connection includes a thread feature 436 on the rotatable sleeve 406 and a thread feature 432 on the inner housing 408. These are best viewed in FIG. 4. In FIG. 4, the thread feature 436 on the rotatable sleeve 406 is male (the groove guide) and the thread feature 432 on the inner housing 408 is female (the groove), although alternatively both thread features 432, 436 may be male or the thread feature 436 may be female and the thread feature 432 may be male.

When the drug delivery device is being dispensed, the user applies an axial load to the dose delivery button 416 located at the proximal end of the mechanism 400. The dose delivery button dose delivery button 416 is axially coupled to the clutch 405 and this prevents relative axial movement. Therefore, the clutch 405 moves axially towards the cartridge end or the distal end of the dose setting mechanism 400. This movement disengages the clutch 405 from the rotatable sleeve 406, allowing for relative rotation while closing up the Gap 'a'. The clutch 405 is prevented from rotating relative to a clicker 420 and hence relative to the inner housing 408. However, in this scenario, the coupling between the first driver portion 407 and the second driver portion 412 is also prevented from becoming disengaged. Therefore, any axial load on the spindle 414 only disengages the first and second driver portions 407, 412 when the dose delivery button dose delivery button 416 is not axially loaded. This therefore does not happen during dispense.

A dose limiter 418 (visible in FIG. 4) is provided on first driver portion 407 and in the illustrated arrangement comprises a nut. The dose limiter 418 has an internal helical groove matching the helical groove of the first driver portion 407. In one preferred arrangement, the outer surface of the dose limiter 418 and an internal surface of the inner housing 408 are keyed together by way of splines. This prevents relative rotation between the dose limiter 418 and the housing 408 while allowing relative longitudinal movement between these two components.

Figure 6:
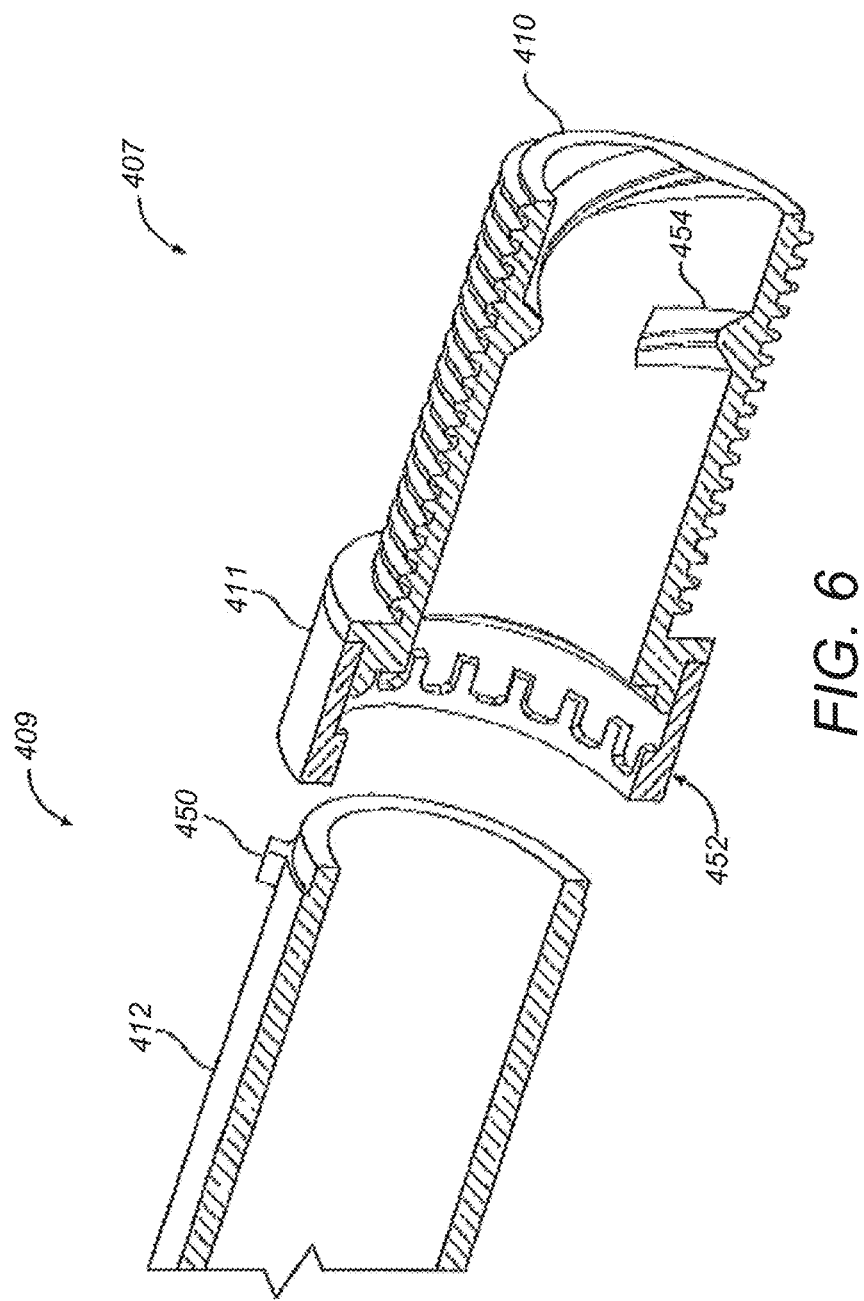
FIG. 6 is an exploded view showing details of a driver forming part of the dose setting mechanism 400 of FIGS. 3 to 5.

FIG. 6 shows in detail a first arrangement of the first driver portion 407 and the second driver portion 412 illustrated in FIGS. 3 to 5. As illustrated in FIG. 6, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart.

In some embodiments, the first driver portion 407 comprises a first portion (first component part) 410 that is permanently clipped to a second portion (second component part) 411. In this arrangement, the second component part 411 comprises the plurality of recesses 452 and the first component part 410 includes the outer groove for the dose limiter 418 nut as well as an internal groove 454. This internal groove 454 is used to connect to the spindle 414 and drives the spindle 414 during dose administration. In the illustrated embodiment, the internal groove 454 comprises a part helical groove, which is easier to manufacture than a complete helical groove.

One advantage of this dose setting mechanism 400 utilizing the inner housing 408 is that the inner housing 408 can be made from an engineering plastic that minimizes friction relative to the rotatable sleeve 406 groove guide 436 and the groove 432. For example, one such engineering plastic could comprise Acetal. However, those skilled in the art will recognize that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The effective driving diameter (represented by 'D') of the grooved interface between the rotatable sleeve 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the encoded member will rotate or lock to the inner body wherein this helix angle is proportional to the ratio of P/D.

A recess 442 in the outer housing 404 of the drug delivery device 100 can be seen in FIG. 3. This recess 442 may be configured to receive an insert or electronic module (not shown), comprising the processor 202, ROM 204, Flash memory 205, RAM 206, display electronics, contacts 212 and batteries 214 previously described. Alternatively, the contacts 212 may be supported at another position on the inner surface of the outer housing 404 and linked to the processor 202 and batteries 214 by conductive paths or wires. The display mount 112 shown in FIG. 1 may be disposed on top of the insert or may be integral with the insert. The display mount 112 is configured to support the display 210. The display 210 may be larger than the recess 442 and may therefore protrude from the outer housing 404. Alternatively, both the display mount 112 and display 210 may be configured to be received by the recess 442 such that the display 210 is flush with the outer surface of the outer housing 404. The contacts 212 are configured to contact the rotatable sleeve 406 in order to facilitate a determination of the rotational position of the rotatable sleeve 406, as will be described in more detail below.

The dose setting mechanism 400 illustrated in FIGS. 3-6 is configured to be re-set to an initial position after the medicament in the attached drug cartridge has been expelled. This allows a new cartridge to be inserted and the drug delivery device 100 to be re-used. This re-setting may be achieved by pushing axially on the distal end of the spindle 414 i.e. the end which usually engages with the drug cartridge and does not require any mechanism associated with removal of a cartridge holder. As illustrated in FIGS. 3 and 4, when the first driver portion 407 is pushed axially towards the second driver portion 412 (i.e., pushed in a proximal direction) the driver 409 is decoupled from the rest of the dose setting mechanism 400.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This will eventually decouple the first driver portion 407 and second driver portion 412.

This axial movement of the first driver portion 407 towards the second driver portion 412 results in certain advantages. For example, one advantage is that the metal spring 401 will compress and will therefore close the Gap 'a' illustrated in FIGS. 3-5. This in turn prevents the clutch 405 from disengaging from the clicker 420 or from the rotatable sleeve 406. The second driver portion 412 is prevented from rotation since it is splined to the clutch 405. The clicker 420 is splined to the inner housing 408. Therefore, when the Gap 'a' is reduced or closed up, the second driver portion 412 cannot rotate relative to either the inner housing 408 or the rotatable sleeve 406. As a consequence, the rotatable sleeve 406 cannot rotate relative to the inner housing 404. If the rotatable sleeve 406 is prevented from rotating then, as the spindle 414 is retracted back into the dose setting mechanism 400 and thereby re-set, there will be no risk of the rotatable sleeve 406 being pushed out of the proximal side of the dose setting mechanism 400 as a result of a force being applied on the spindle 414.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 3-6 into a non-resettable drug delivery device, the first component part 410 and the second component part 411 of the first driver potion 407 and the second driver portion 412 can be moulded as one unitary part. This reduces the total number of drug delivery device components by two. Otherwise, the drug delivery device illustrated in FIGS. 3-6 could remain unchanged. In such a disposable device, the second housing part 106 would be fixed to the first housing part 104 or alternatively made as a single one piece body and cartridge holder.

The dose setting mechanism described above is merely one example of a mechanism suitable for supporting the rotatable sleeve 406 and for implementing the present invention. It will be apparent to the skilled person that other mechanisms may also be suitable.

In view of the foregoing it will be appreciated that a user twists the rotatable dial 108 to select an amount of dose to be dispensed from a drug cartridge. This causes the rotatable sleeve 406 to rotate and translate axially (longitudinally) relative to the housing 102. By analysing information that relates to rotation of the rotatable sleeve 406 the extent of rotation of the dial 108, and thus the dose dialled, can be determined. Furthermore, a user presses the dose delivery button 416 to dispense an amount of dose from within a drug cartridge. Pressing the dose delivery button 416 causes the rotatable sleeve 406 to rotate and move axially the other way. Thus by analysing information that relates to rotation of the rotatable sleeve 406, the dose dispensed can also be determined.

A number of schemes for determining an amount of rotation of a sleeve, typically called an encoder sleeve or a number sleeve, are possible. Some possible schemes involve a conductive pattern formed on the cylindrical outside surface of the sleeve. Here, electrical contacts mounted in a fixed position relative to the main housing may be caused to contact different parts of the pattern as the sleeve moves within the main housing. By examining signals provided at the contacts by connection (or no connection) with the pattern, the location of the sleeve within the main housing might be determined, or at least estimated. In other schemes, a pattern on an encoder sleeve may be read optically. Reference is made to the prior art for specific details of known mechanisms and schemes.

Embodiments of the present invention propose a different scheme. In brief, a conductive pattern formed on the cylindrical outside surface of the sleeve is not used. Instead, a conductive pattern is formed on an engaging face of thread features of a body component or a sleeve and contacts are provided on the other component. Apparatus so constructed can allow determination of the relative position of the sleeve and the body component through detecting the conductive track pattern whilst providing no or relatively little additional resistance to axial movement of the body component relative to the sleeve compared to a corresponding arrangement in which the conductive track and contacts were absent. In schemes using a conductive pattern formed on the cylindrical outside surface of the sleeve, conversely, friction forces resulting from contacts sliding over the conductive patter as the sleeves rotates on the inner body can provide significant additional resistance to axial movement of the body component relative to the sleeve.

Figure 7:
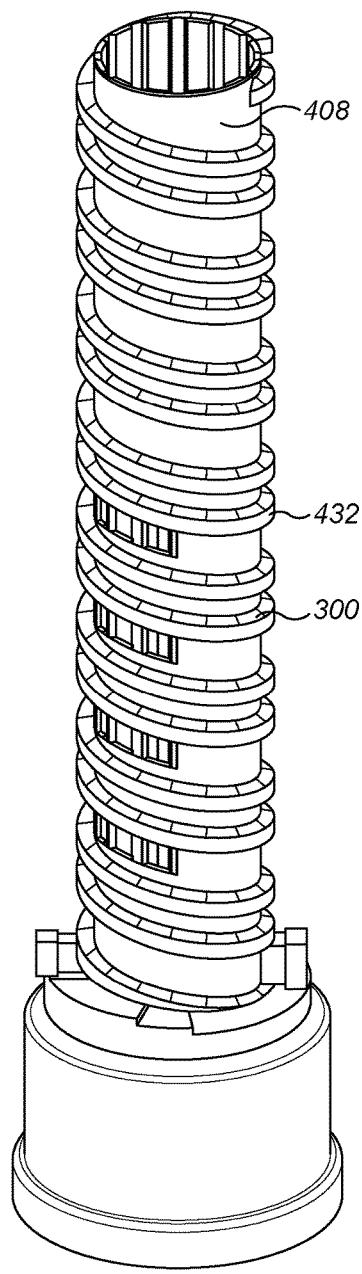
FIG. 7 is a perspective view of an inner housing forming part of a first embodiment of the present invention.
Figure 8:
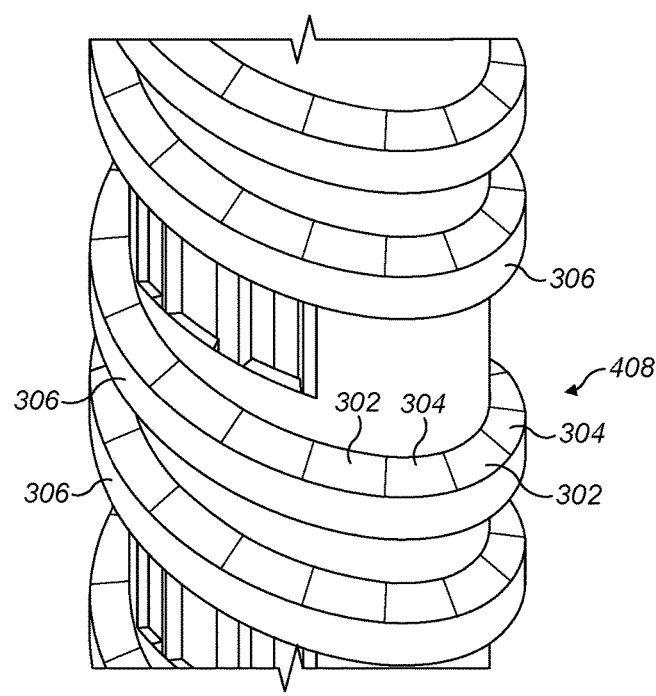
FIG. 8 is a detailed view of part of the inner housing of FIG. 7.

Referring now to FIGS. 7 and 8, a first set of embodiments will be described. Here, the inner housing 408 is shown in perspective view. FIG. 7 is a view of the whole of the inner housing 408 and FIG. 8 is a magnified view of a part of the inner housing. In both FIGS. 7 and 8, a thread feature 432 is clearly visible on the external surface. This thread feature 432 is a twin start thread.

The thread feature 432 includes three main faces. A first face faces upwardly in the figures, and can be called an engaging face 710. Opposite the engaging face 710 is a bottom face 714, which is not visible in FIGS. 7 and 8 because of the angle of view of these figures but are visible in FIG. 13. Connecting the engaging face 710 and the bottom face 714 is a side face 712. The side face 712 is generally concentric with the main face of the inner housing 408. The engaging face 710 and the bottom face 714 may be perpendicular to the axis of the inner housing 408. Alternatively, they may be angled slightly, in particular they may be angled such that the angle at the intersection between the engaging face 710 and the side face 712 is slightly greater than 90 degrees, for instance around 95 degrees. Correspondingly, the angle of intersection between the engaging face 710 and the main external face of the inner housing 408 may be slightly greater than 90 degrees, for instance 95 degrees. The same applies to the angle of the bottom face 714. There are two benefits from having a flank angle on these threads. The first is functional in that the angle acts like a cone to help keep the components concentric and make the designed sections of the threads contact, not the cylindrical surfaces etc. The second is that it simplifies manufacturing of the components (e.g. by injection moulding).

A helical track 300 is provided on the thread feature 432 on the inner housing 408. The helical track 300 comprises a number of components. Firstly, a connecting track 306 is provided on the side face 712 of the thread feature 432. The connecting track 306 is continuous, that is it is unbroken.

The helical track 300 includes some features on the engaging face 710 of the thread feature 432 of the inner housing 408. These include alternating conductive segments 302 and non-conductive segments 304. The conductive segments 302 are electrically coupled to the connecting track 306, that is located on the side face 712 of the thread feature 432. Successive conductive segments 302 are separated by a non-conductive segment 304. Similarly, successive non-conductive segments 304 are separated by a conductive segment 302.

As will be described, when a contact 212 is mechanically coupled to a conductive segment 302, an electrical circuit is made between the contact and the connecting track 306. When the contact 212 is mechanically coupled only to a non-conductive segment 304, no electrical circuit is made between the contact 212 and the connecting track 306.

Figure 9:
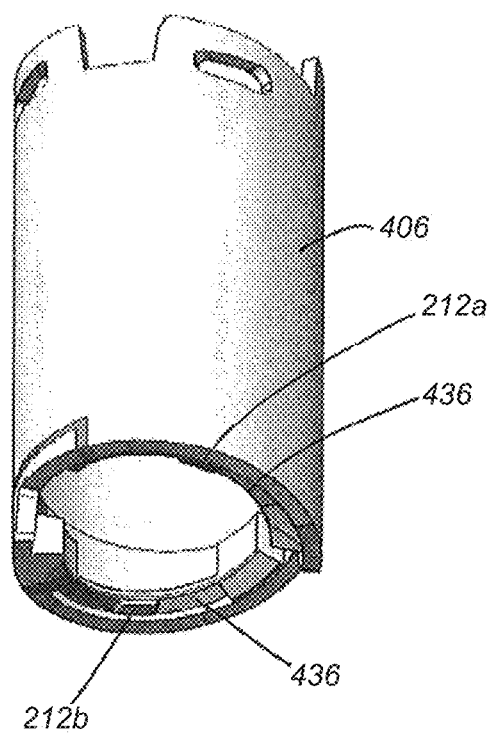
FIG. 9 is a perspective view of a rotatable sleeve forming part of the first embodiment.
Figure 10:
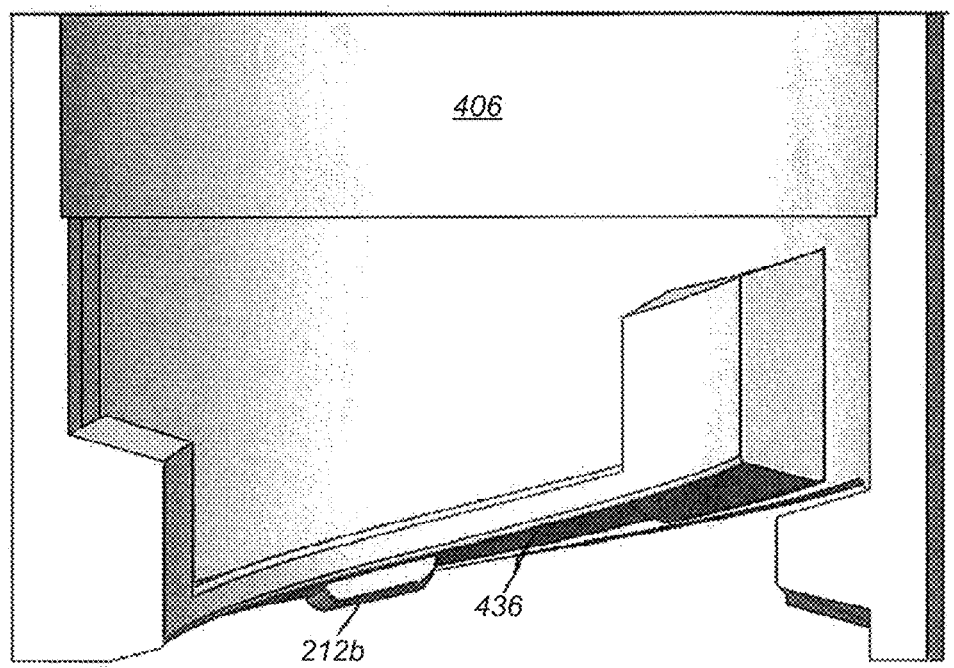
FIG. 10 is a cross-section of a part of a rotatable sleeve of FIG. 9.

The contacts 212 form part of the rotatable sleeve 406, as will now be described with reference to FIGS. 9 to 11.

Referring to these figures, the rotatable sleeve 406 is shown as comprising a generally annular component, with some features at each end. The features at the top end are not of relevance to this explanation, so will not be described.

At the lowermost end of the rotatable sleeve 406 are provided thread features 436. The thread features 436 comprise sections of a twin start thread having the same pitch and direction as the thread components 432 on the inner housing 408. The thread features 436 are provided with an engaging face 716, which is downwardly facing in the figures. In use, the engaging face 716 of the thread features 436 of rotatable sleeve 406 is engaged with the engaging face 710 of the thread features 432 of the inner housing 408.

First and second contacts 212a and 212b are formed on the engaging face 716 of the thread feature 436 of the rotatable sleeve. The contacts 212a and 212b are formed on different ones of the twin start threads, so engage with different ones of the twin start threads features 432 of the inner housing 408 in use.

The contacts 212a, 212b comprise flat-topped protrusions that extend from the generally regular surface that constitutes the engaging face 716 of the thread feature 436 of the rotatable sleeve 406. They may alternatively take the form shown in and described below with reference to FIG. 15.

Figure 11:
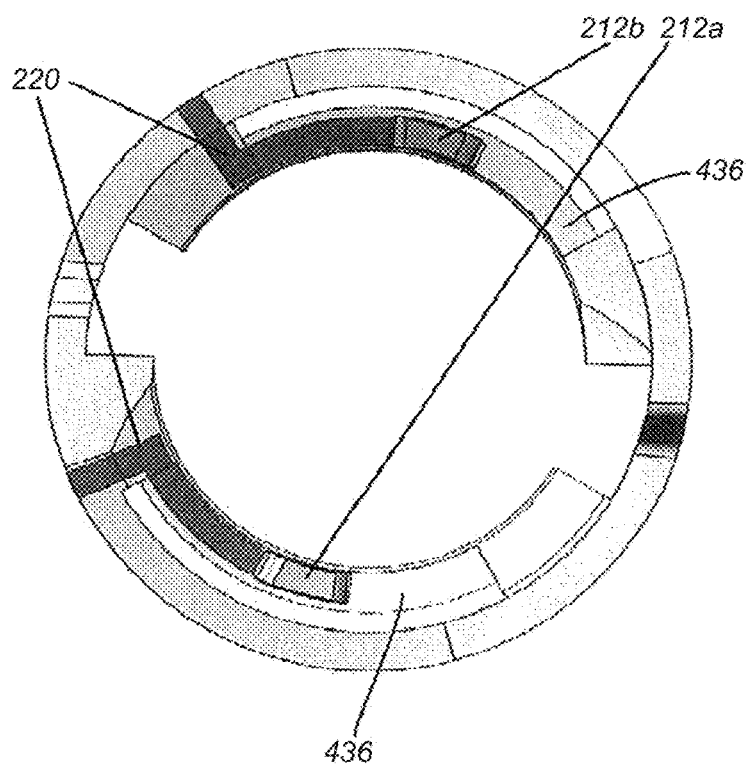
FIG. 11 is an end view of the rotatable sleeve of FIG. 9.

A conductive track 220 commences on the face of the contacts 212a, 212b and extends for some distance along the engaging face 716 of the thread feature 436 of the rotatable sleeve 406, before extending off of the engaging face, as is best seen in FIG. 11.

Figure 12:
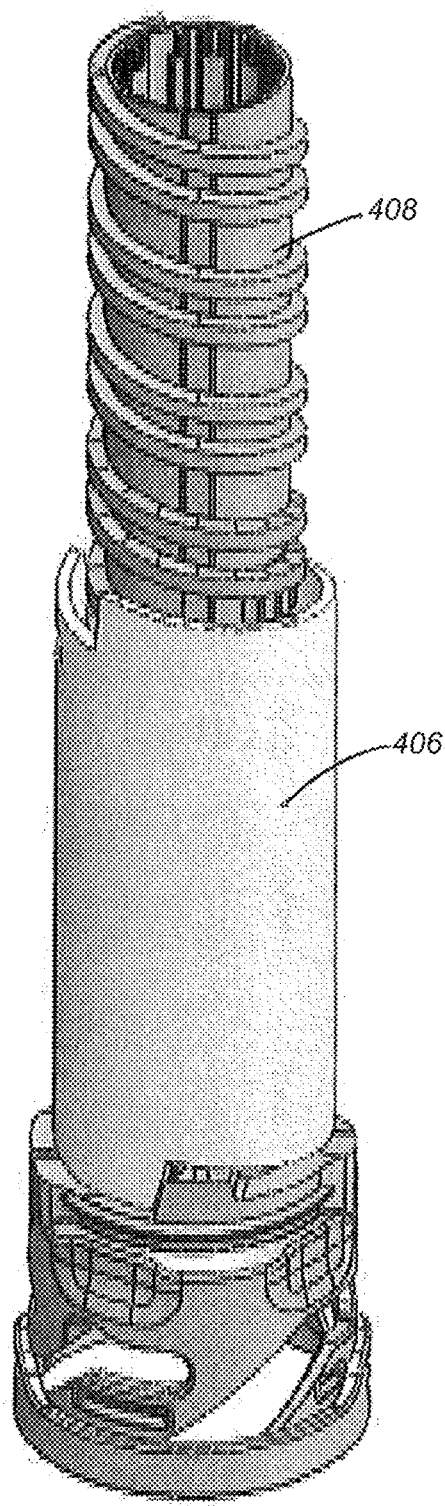
FIG. 12 is a perspective view of the rotatable sleeve of FIGS. 9 to 11 installed on the inner housing of FIGS. 7 and 8.

FIG. 12 shows the rotatable sleeve 406 installed on the inner housing 408. From FIG. 12, it can be seen that the rotatable sleeve 406 is considerably shorter than the inner housing 408 so, even when the rotatable sleeve 406 is fully wound onto the inner housing 408 such that it rests at the bottom thereof, a significant part of the inner housing 408 extends out of the top of the rotatable sleeve 406.

Figure 13:
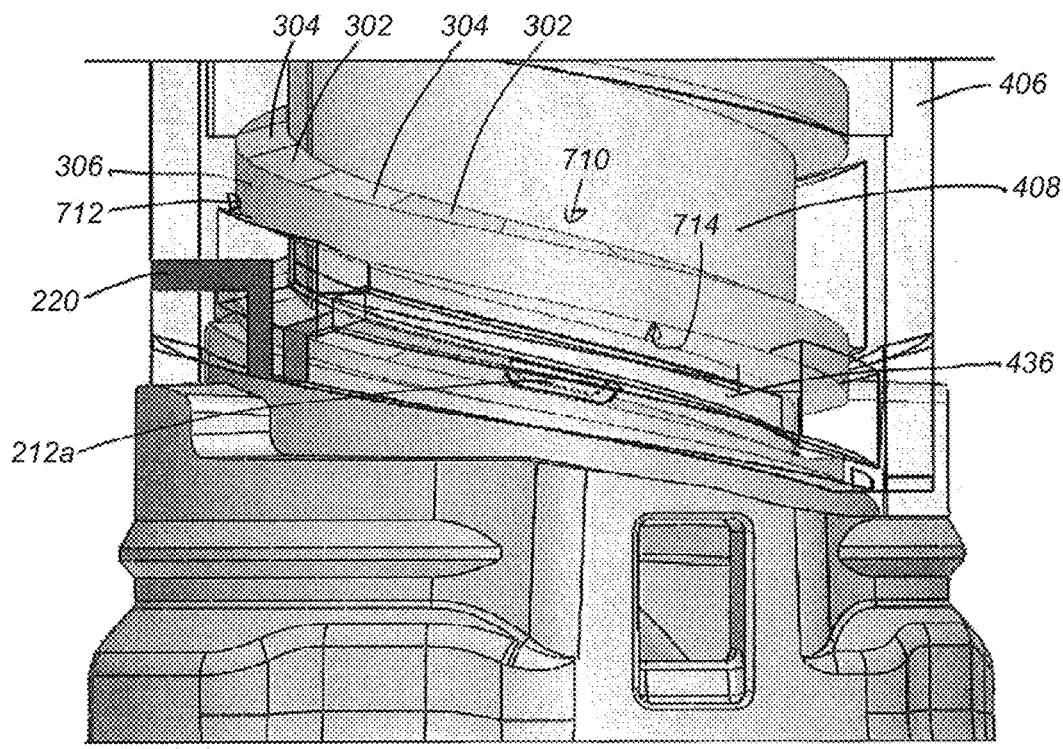
FIG. 13 is a detailed side view of part of the apparatus shown in FIG. 12, with the rotatable sleeve in wireframe.

The relative positions of some of the components of the rotatable sleeve 406 and the inner housing 408 when the components are engaged with one another are shown in FIG. 13. Here, it can be seen clearly that the thread feature 436 of the rotatable sleeve 406 corresponds closely with the thread feature 432 of the inner housing 408. Furthermore, the engagement of the first contact 212a on the part of the helical track 300 that includes the conductive segments 302 and the non-conductive segments 304 is clearly visible. FIG. 13 also shows also how the connecting track 220 extends from the exterior of the rotatable sleeve 406 to the first contact 212a.

Although not shown in the Figures, the ends of the connectors on the inner housing 408 are accessible through a hole in the outer housing 404 and are electrically connected to the encoder 202 or provide an interconnect for a separable module. Because the inner housing 408 also is fixed to the outer housing 404, the tracks may pass through with a rigid connection to more interconnecting tracks on the housing to pass to the encoder 202 directly or through an interface to a separate module.

The connecting track 220 on the rotatable sleeve 406 does not connect to the encoder 202, but it does connect the two contacts together. The track 220 that is leftmost as shown in FIG. 13 runs round the outer diameter to the other contact. This is represented in FIG. 14 as the bottom line connecting sleeve contacts 212a and 212b, i.e. not connecting to the encoder 202.

The contacts 212a and 212b are sprung, as will be described below with reference to FIG. 15.

The helical tracks 300 shown in FIGS. 8 to 13 are identical on both threads of the twin start thread feature 432. Although the first and second contacts 212a and 212b are distributed around the circumference of the rotatable sleeve 406, they contact corresponding parts of the helical track 300 on their respective thread. As such, the first and second contacts 212a, 212b are either both in contact with a conductive segment 302 of their respective helical track 300 or are both in contact with a non-conductive segment 304 of the helical track 300. Put another way, signals detected by both contacts are identical.

Figure 14:
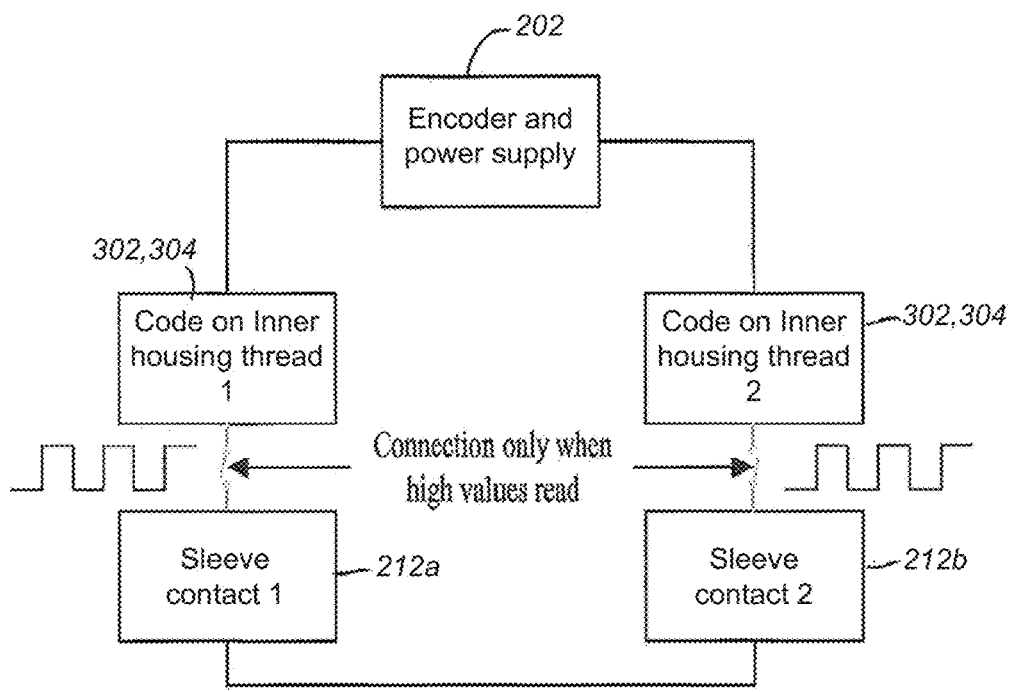
FIG. 14 is a schematic illustration of an electrical circuit that is included in the first embodiment.

An electrical circuit suitable for use with this particular arrangement is shown in FIG. 14.

Here, an encoder and power supply is provided by the processor 202 in conjunction with the battery 214, both of which are shown in FIG. 1. On the left side of FIG. 14, a code 302, 304 on a first thread feature 432 of the inner housing 408 is coupled to the first contact 212a on the rotatable sleeve 406 when the contact 212a is aligned with a conductive segment 302. This is represented by a switch between the two components in FIG. 14.

Similarly, on the right side of the figure the code 302, 304 on the second of the twin start thread features 432 connects the contact 212b on the second thread of the rotatable sleeve 406 to the encoder and power supply 202 when a conductive segment 302 is in contact with the contact 212b.

The height of the thread features 436 on the rotatable sleeve 406 is such that the sprung contacts 212a and 212b provide a pre-load force between the bottom face 714 of one thread feature 432 of the inner housing and the engaging face 710, or uppermost face, of the other thread feature 432 of the inner housing 408. When the dose delivery button is not pressed, this pre-load force provides adequate pressure to the first and second contacts 212a and 212b to achieve electrical connection between the connecting tracks 220 and the helical track 300 when the contacts 212a and 212b coincide with a conductive segment 302 of the helical track 300.

Figure 15A:
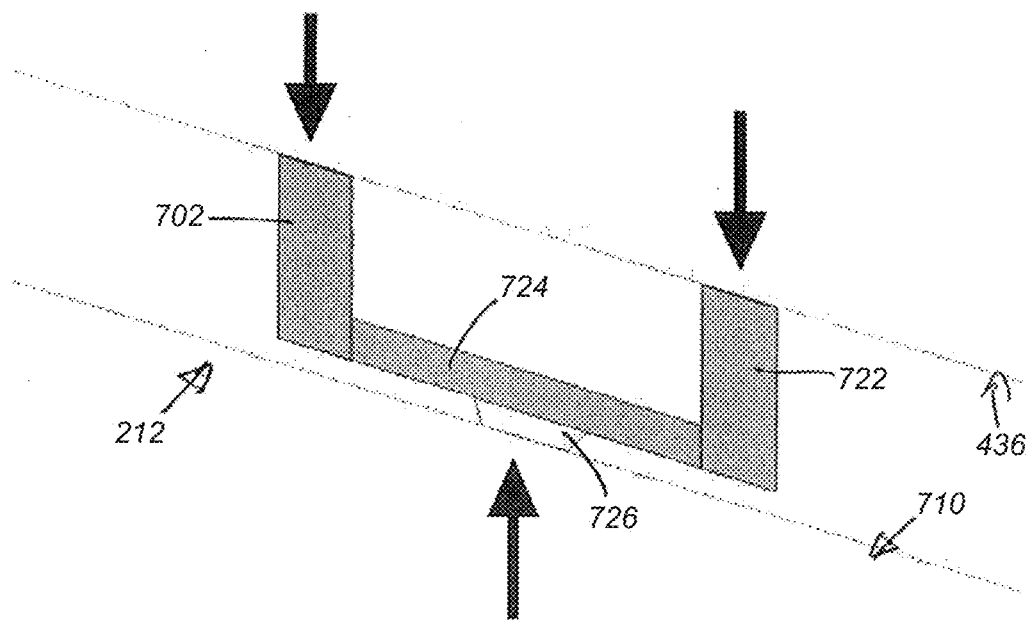
FIG. 15a is a schematic drawing of a contact forming part of the first embodiment.
Figure 15B:
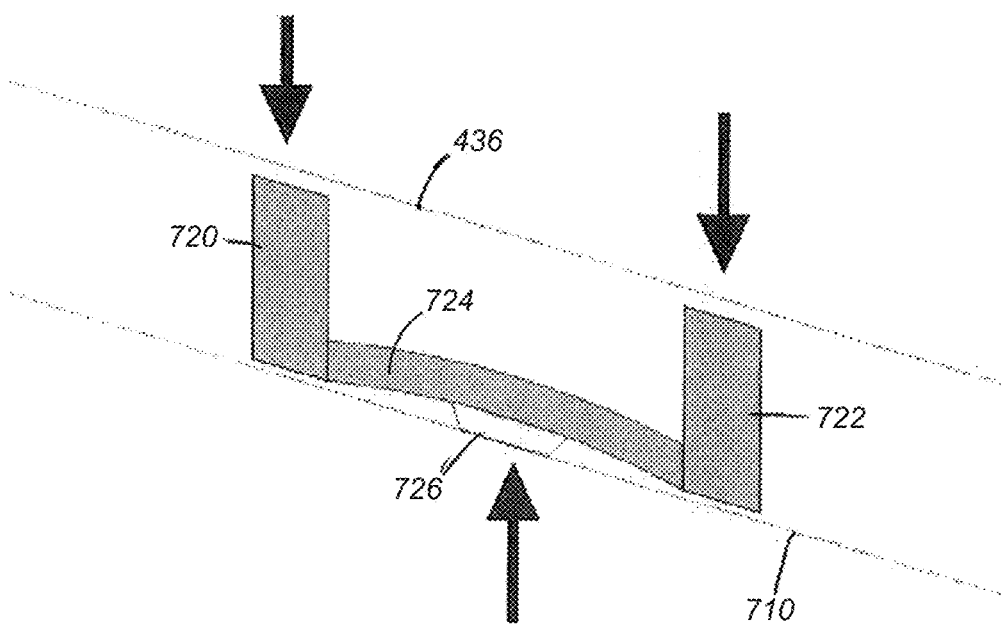
FIG. 15b is the contact of FIG. 15a in a dose dialling operation.

For instance, the contacts 212a and 212b may take the form shown in FIGS. 15a and 15b. These are schematic figures, but show the functionality provided by the contacts. They show a contact 212 comprising a beam 724 supported at two ends by a first support 720 and a second support 722. A contact pad 726 is supported in the middle of the beam 724 on a face that is opposite to the first and second supports 720, 722. It is the contact pad 726 that contacts the helical track 300 in use.

FIG. 15a shows the contact 212 during a dialling operation. During dialling, a user manipulates the dialling knob 108 to dial in a dose into the injection pen 100. During dialling, the delivery button is not pressed. During dialling, the preload ensures that adequate pressure is applied to the contacts 212 to achieve conductivity with the helical track 300.

FIG. 15b shows the contact 212 during a dose delivery, or dose dispensing, operation. In this operation, the dose delivery button is depressed. Here, the thread feature 432 of the inner housing 408 causes the rotatable sleeve 406 to rotate as it travels helically in a distal direction within the main body 102. A certain axial force needs to be applied to the inner housing 408 in order to overcome friction between the thread feature 436 of the rotatable sleeve 406 and the thread feature 402 of the inner housing 408 before relative motion will begin. As the dose delivery button is depressed, the preload force acting on the thread feature 432 of the inner housing 408 and the thread feature 436 of the rotatable sleeve 406 is reduced and this force is instead transferred to the dose delivery button. As such, there is no additional force during dispensing resulting from the frictional force between the contact 212 and the helical track 300 compared to a corresponding arrangement in which the contacts 212 and the helical tracks 300 were not present. There may, of course, be some difference in the frictional force that needs to be overcome before relative movement can occur due to differences in the materials that move over one another. However, even if the additional friction resulting from the choice of materials is significant, the friction that would result from having a contact and conductive track arrangement on a cylindrical surface of a rotatable sleeve would be expected to be significantly higher.

If the preload force is less than or equal to the axial force required to rotate the rotatable sleeve 406, the preload force is completely removed during the dispense operation. If the preload force is greater than the dispense force, there is nonetheless a benefit provided by the described arrangement because the axial force during the dispense operation is in effect subtracted from the preload force, giving a lower force than if the preload force was applied independently.

The helical tracks 300 described above implement an incremental code. The track alternates between conductive "high" values and "low" values. The encoder 202 counts the number of output changes, namely high to low and low to high, to calculate the dialled dose. This approach has fundamental limitations as the encoder 202 is not able to determine whether the device 100 is dialling or un-dialling a dose. Furthermore, incremental coding is not able to determine if the encoder 202 has failed to register dialled units.

Alternative implementations, using different helical tracks 300, can overcome these shortcomings, as is described below.

Firstly, some variations of and modification to the above-described embodiment will now be discussed.

Instead of including the connecting track 306 of the helical track 300 on the side face 712 of the thread feature 432 of the inner housing 408, it may be otherwise provided. For instance, it may be provided on the major face of the inner housing 408, at the part that is closest to the engaging face 710 of the thread feature 432 for example. It may alternatively be provided on the bottom face 714 of the thread feature 432, in which case connecting tracks may extend around the side face 712 to connect the conductive segments 302 on the engaging face 710 with the connecting track 306 on the bottom face 714.

The thread features 432 and 436 need not be twin start threads. They may alternatively be single start threads, or triple or higher order start threads.

Instead of the relatively long thread feature being provided on the inner housing 408, it may instead be provided on the innermost surface of the rotatable sleeve 406. In this case, the inner housing 408 is provided with a thread feature on its outermost surface. However, this need not be continuous, and may be relatively short or may be plural sections of partial thread.

In a second set of embodiments, that will now be described with reference to FIGS. 16, 17 and 18, a different coding technique is used. In the following, as throughout the specification, like reference numerals refer to like elements. Additionally, the below-described embodiments include all of the features of the above-described embodiments unless otherwise stated.

Figure 16:
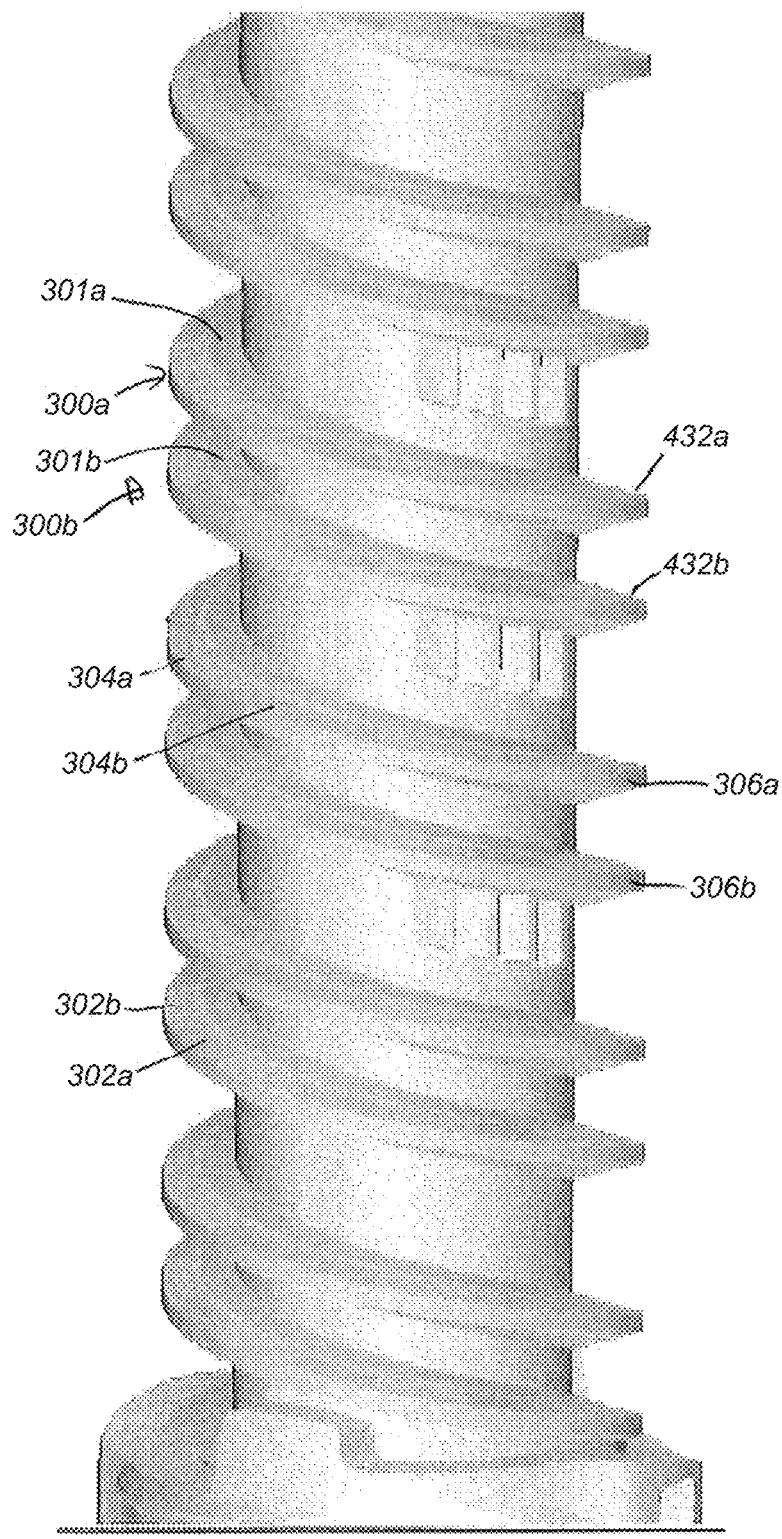
FIG. 16 is an inner housing used in a second embodiment.

As shown in FIG. 16, each of the two thread features 432 of the inner housing 408 is provided with a different helical track 300. Here, the thread feature 432 includes a first thread 432a and a second thread 432b. A first helical track 300a is formed on the first helical thread feature 432a. A second helical track 300b is formed on the second thread feature 432b. A first helical power track 301a is formed on the first helical thread feature 432. A second helical power track 301b is formed on the second thread feature 432b. The power tracks 301a, 301b provide electrical power to the system, and their utility is particularly apparent from FIG. 18.

As with the helical track 300 of the first set of embodiments described above, each helical track 300a, 300b includes conductive segments 302a and 302b and non-conductive segments 304a and 304b. Each helical track 300a, 300b also includes a respective connecting track 306a, 306b. The second helical track 300b has the same alternating code as used in the examples above. Where number 1 represents high values and number 0 represents low values, the code of the second helical track 300b may be represented as:

0101010101010101

The first helical track 300a has the following code:

001100110011

The combinations of these two codes produces a repeating sequence of four unique outputs, as follows:

00,10,01,11,00,10,01,11

Figures 17, 18:
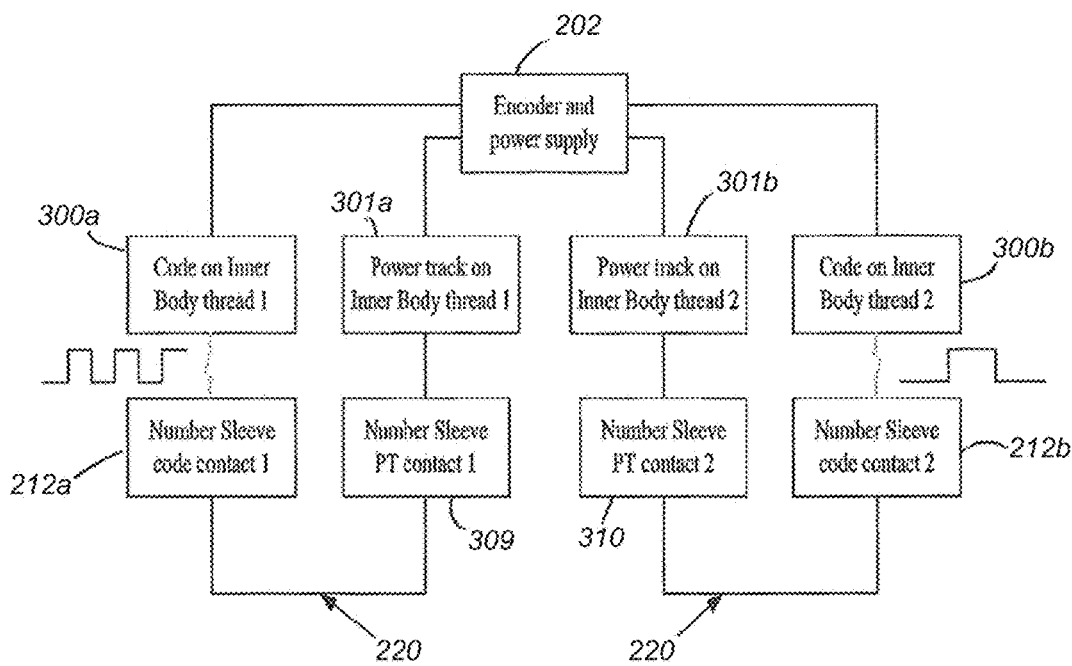
FIG. 17 illustrates a code present on the inner housing of FIG. 16 and outputs at different positions of the contacts on the code.
FIG. 18 is a schematic diagram illustrating electrical circuits present when the inner housing of FIG. 16 is used in the second embodiment.

This is illustrated in FIG. 17, where the repeating sequence can be seen to be derived from consecutive locations on the helical tracks 300a, 300b.

The code can be read by the circuit shown in FIG. 18. Here the encoder and power supply 202 has four inputs. At the left side, a connection is made between the code 302a, 302b on the first thread feature 432a and a first contact 212a on the rotatable sleeve 406. A connection is made back to the encoder 202 by way of the connecting track 220 on the number sleeve and a first power track contact 309, via the connecting track 306a of the helical track 300. The power track contact 309 contacts the first power track 301a.

On the right side of FIG. 18, a circuit is provided to and from the encoder by the conducting and non-conducting segments 302b, 304b of the second helical track 300b to the second contact 212b of the number sleeve 408, via the connecting track 220 on the number sleeve 408 and a second power track contact 310 and the second connecting track 306b of the second helical track 300. The second power track contact 310 contacts the second power track 301b.

It will be appreciated that this does not provide absolute encoding but it does have some advantages over the purely incremental code used in the previous embodiments. Particularly, since there are four different outputs of the arrangement, as shown in FIG. 17, the encoder 202 can determine whether the device 100 is dialling or un-dialling. In particular, this can be determined from the direction in which the sequence is moving.

Additionally, if the injection device 100 has been dialled quickly and some of the dialled units have been missed or misread by the encoder 202, the encoder 202 may be able to determined that the dialled dose is incorrect. In this case, the device 100 may indicate to the user to restart dialling. A user can perform this by dialling the dose back down to zero and then again commencing the dialling. The system is not completely error proof because a mis-read by a factor of 4 (which is the period of repeat of the code) would seem to the encoder 202 to be correct.

Some variations of and modification to this embodiment will now be discussed.

Although in the above, the code that is provided by the helical tracks 300a, 300b is a conventional binary code, it may instead be provided by a Gray code. The use of a Gray code has an advantage that the chances of mis-reading in a transition where two (or more) bits of the code change is reduced. Referring to FIG. 17, for instance, changing between dial position 2 and dial position 3 involves a change of the code from 10 to 01, that is both of the bits change. With a Gray code, conversely, only one of the bits changes when the dial position increments or decrements.

Instead of including the connecting tracks 306a, 306b of the helical track 300 on the side faces 712a, 712b of the thread features 432 of the inner housing 408, they may be otherwise provided. For instance, they may be provided on the major face of the inner housing 408, at the part that is closest to the engaging face 710 of the thread feature 432 for instance. They may alternatively be provided on the bottom face 714 of the thread feature 432, in which case connecting tracks may extend around the side face 712 to connect the conductive segments 302 on the engaging face 710 with the connecting track 306 on the bottom face 714.

The thread features 432 and 436 need not be twin start threads. They may alternatively be single start threads, or triple or higher order start threads.

Instead of the relatively long thread features 432a, 432b being provided on the inner housing 408, they may instead be provided on the innermost surface of the rotatable sleeve 406. In this case, the inner housing 408 is provided with a thread feature on its outer most surface. However, this need not be continuous, and may be relatively short or may be a number of short sections of partial thread.

Also, although it is the sleeve 406 that rotates and the inner housing 408 is fixed relative to the main body 102, it may instead be the inner housing 408 that rotates and the sleeve 406 may be fixed relative to the housing 102.

A third set of embodiments will now be described with reference to FIGS. 19 to 25.

In this embodiment, seven different parts of a code are read by seven different contacts 212. Outputs from the seven contacts 212 are then assembled to produce a seven-bit code by the encoder 202. An example of the code is shown below.

10000011000010100001110001001000101100011010001111100100110010101001011100110011001110100

This translates to the output shown in FIG. 19. Here, the code is shown extending down the page. Contacts provided at the first seven consecutive bits in the leftmost column read off a code 1000001. Once the contacts have been incremented, the output read off the code, which is shown in the middle column, is 0000011. After moving one further step, the code read off of the contacts is shown in the right column as 0000110. The code is constructed such that the dialled dose can be uniquely identified up to an 80 unit maximum dose by examining signals provided at the contacts 212. Put another way, the signals provided at the contacts 212 uniquely identify a dose in the range of 0 to 80 units.

In this example, the contacts 212 are located at seven consecutive bits of the code, which is formed by the conductive segments 302 and the non-conductive segments 304 of the helical track 300. Alternatively, the contacts 212 may be located to contact different parts of the code, some or all of which may be non-consecutive, as is described below with reference to FIG. 26.

A seven bit code allows determination of a unique number between 0 and 128, which is sufficient for determining a dialled dose in the range of 0 to 80. Having a shorter code, for instance 6, 5 or 4 bits, simplifies the apparatus (at least because there are fewer contacts), although it allows a smaller range of dialled dose units to be uniquely identifiable. Nevertheless, using a shorter code may be preferred in some embodiments.

The greater the number of contacts 212, the more difficult it is technically to include the contacts on the inner housing 408.

Figure 20:
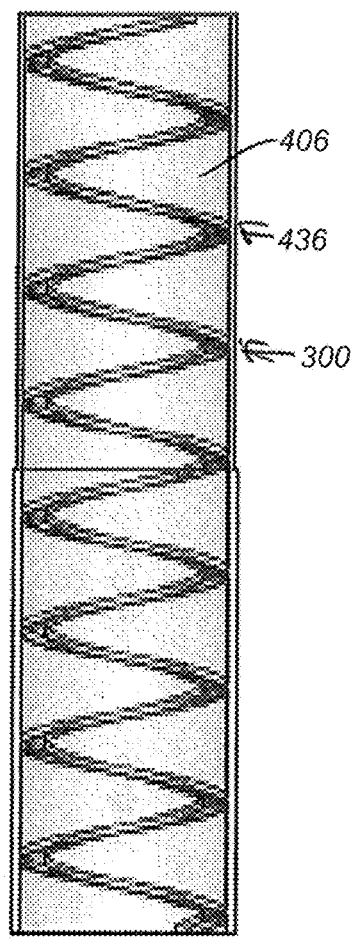
FIG. 20 is a side view of a rotatable sleeve according to a third embodiment of the invention, in a partially wireframe.
Figure 21:
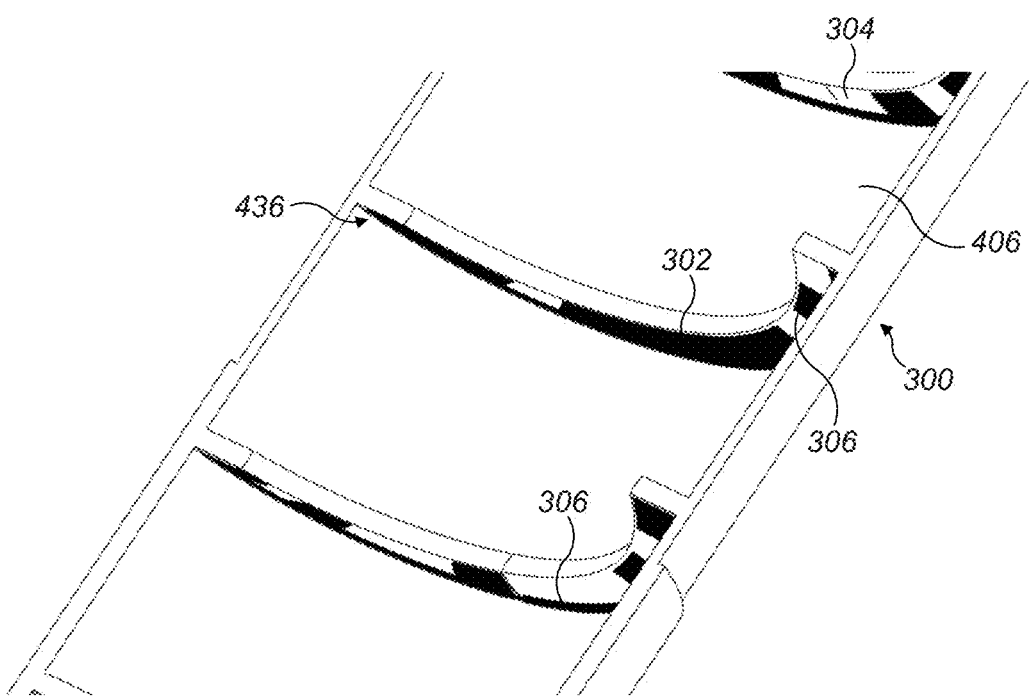
FIG. 21 is some detail of the rotatable sleeve of FIG. 20.

As is best seen from FIGS. 20 and 21, which show the rotatable sleeve 406 in wireframe so that internal details are visible, the thread feature 436 is provided on the inside surface of the rotatable sleeve 406.

Here, it is a single start thread 426. It includes a helical track 300, that extends for a significant part of the length of the thread feature 436. The thread feature 436 includes three main faces. The engaging face 716 is the lowermost face in the figures. This is opposite to the engaging face 716 in the previous embodiment because in this embodiment it is the lowermost face of the thread feature 436 that provides a reactive force against the corresponding thread feature 432 of the inner housing 408, particularly when a dose is being delivered. An uppermost face 714 is opposite the engaging face 710. As with the above embodiments, the engaging face 710 and the uppermost face 714 may be angled slightly from perpendicular with the axis of the device 100. A side face 712 connects the engaging face 710 and the bottom face 714. The side face 712 is generally concentric with the outer cylindrical surface of the inner housing 408.

The connecting track 306 of the helical track 300 is provided on the engaging face 710 of the thread feature 432 The connecting track 306 is shown in the Figures as a very thin connection running along the engaging face 710. The conductive segments 302 and non-conductive segments 304 are provided on the engaging face 710, which is the lowermost face, of the thread feature 432.

Clearly visible in FIG. 21 is the fact that the code does not comprise consecutive conductive segments 302 and non-conductive segments 304 of the same length. Instead, some of the conductive segments 302 and the non-conductive segments 304 relate to two or more consecutive bits of the same value.

Figure 22:
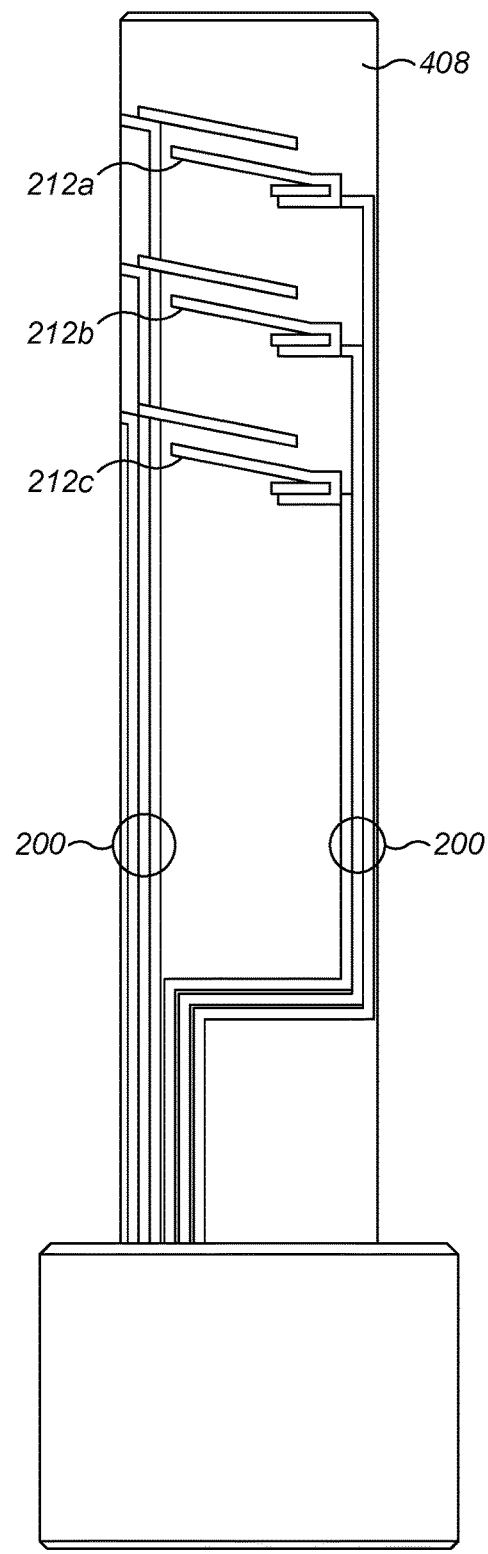
FIG. 22 is a side view of an inner housing forming part of the third embodiment and used with the rotatable sleeve of FIGS. 20 and 21.

The inner housing 408 is provided with contacts 212. In particular, seven contacts 212 are provided on the inner housing 408 in contact with the helical track 300. First to third contacts 212a, 212b and 212c are shown in FIG. 22. Also shown in FIG. 22 is connecting track 220 that connects the contacts 212a to 212c and other contacts (not shown in the figure because they are on the reverse side of the inner housing 408 as shown) to the bottommost end of the inner housing 408.

Figure 23:
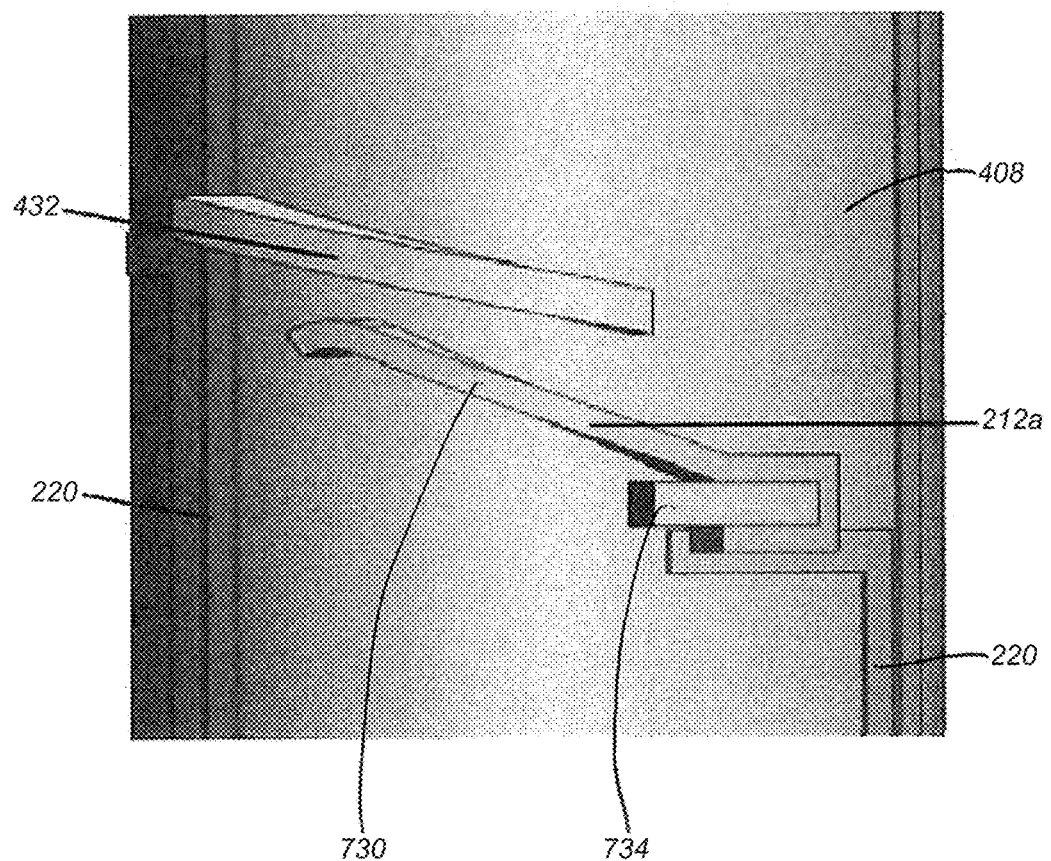
FIG. 23 is a detail of a part of the inner housing of FIG. 22, showing a contact and a thread feature.

All of the contacts 212 are substantially the same, and the first contact 212a is shown in detail in FIG. 23.

Here, it can be seen also that a thread feature 432 of the inner housing 408 comprises a part of a thread. The thread feature 432 provides a part of a thread that has the same pitch as the thread 436 on the rotatable sleeve 406.

The contact 212a comprises an arm 730. The arm is supported at one end on a support 734. The arm 730 is connected to the connecting track 220 at the location of the support 734, in this example on the underside of the support 734. The support 734 is provided by a protrusion that extends from the main cylindrical body of the inner housing 408.

At the opposite end to the support 734, the arm 730 has a free end 732. It is the free end 732 of the arm 730 that contacts the helical track 300 in use.

The arm 730 is resilient, and is biased into the position shown in FIG. 23. The arm 730 may be made of a metal, for instance. The arm 730 provides an electrical connection between the connecting tracks 220 and the conductive segments 302 of the helical track 300 in use.

Figure 24:
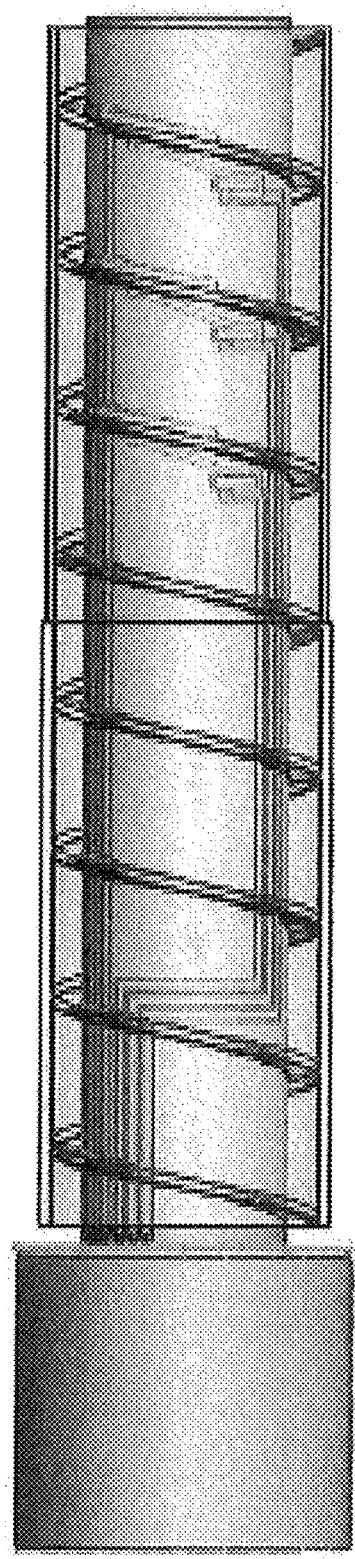
FIG. 24 is a side view of the rotatable sleeve of FIGS. 20 and 21 in wireframe installed on the inner housing of FIGS. 22 and 23.
Figure 25A:
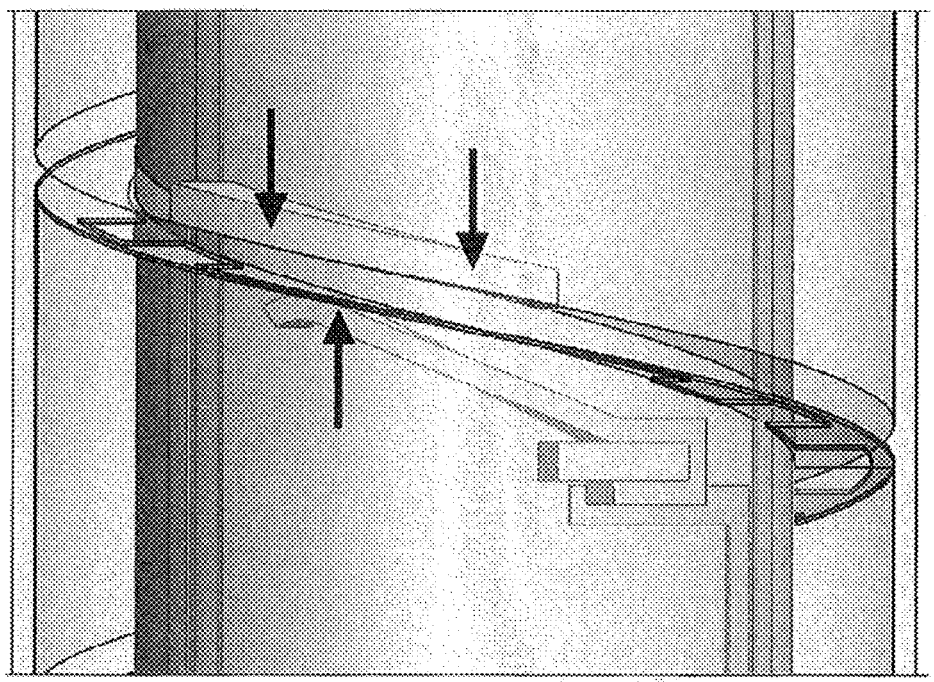
FIG. 25a is some detail of the apparatus of FIG. 24, when in a dialling mode.
Figure 25B:
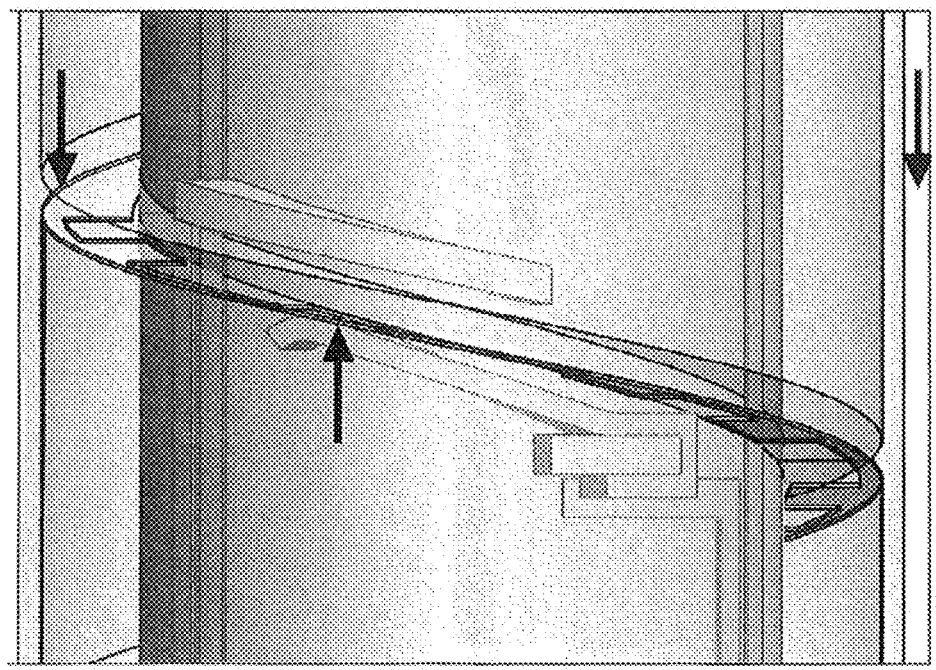
FIG. 25b is the same part of the apparatus as is shown in FIG. 25a, although in a dose delivery mode.

FIG. 24 shows the rotatable sleeve 406 in wireframe located on the inner housing 408. In FIG. 24, the thread feature 432 of the inner housing 408 is engaged with the thread feature 436 of the rotatable sleeve 406. Some details of this are shown in FIGS. 25a and 25b.

The distance between the thread features 432 and the free end 732 of the arm 730 is such that the contacts 212 provide preload forces acting on the thread features 436 of the rotatable sleeve 406 in use. This is represented by the arrows in FIG. 25a. This Figure shows the relative positions between the rotatable sleeve 406 and the inner housing 408 during a dialling operation, or when the injection device 100 is not in use. As can be seen, the uppermost face 714 of the thread feature 436 of the rotatable sleeve 406 is in contact with the lowermost face of the thread feature 432 of the inner housing 408. In this position, the preload force ensures that adequate pressure is applied to the helical track 300 by the contact 212 to achieve conductivity therebetween, which therefore enables the encoder 202 to determine whether the contact 212 is in connection with a conductive segment 302 or a non-conductive segment 304 and, with the outputs from the other contacts 212, determine the position of the rotatable sleeve 406 relative to the inner housing 408.

During dispensing a dose, the thread feature 436 of the inner housing 408 causes the rotatable sleeve 406 to rotate as it travels helically in a distal direction. Due to friction between the thread feature 436 and the thread feature 432, an axial force must be applied to the inner housing 408 for relative motion to occur. As the force applied to the dose delivery button is applied to the inner housing 408, the preload force acting on the thread features 432, 436 is reduced and this force is instead transferred to the dose delivery button. This is illustrated by the arrows in FIG. 25b, which relates to a dose dispensing mode. During dose dispensing, the transference of the preload force to the dose delivery button means that there is no additional force required by the presence of the contacts 212 and the helical track 300 compared to a corresponding arrangement absent of contacts and a helical track in the manner shown, subject to any differences that might be experienced resulting from different materials at the point of contacting.

When a user of the device 100 twists the rotatable dial 108 to select or dial in a drug dose, the processor 202 may be activated and may be controlled by software stored in the ROM 204 to execute a check on the contacts 212*a* to determine the absolute rotational position of the rotatable sleeve 406, and hence the drug dose which has been dialled. The processor 202 may also be configured to determine the number of drug units which have been delivered.

The process of determining a dialled dose will now be described. In order to determine the drug dose which has been dialled, the processor 202 first causes the batteries 214 to apply a voltage to all contacts 212 that are needed to read the code from the helical track or tracks 300. The processor then uses signals received at other inputs to determine which of the contacts 212 are in contact with conducting portions 302 and which are in contact with non-conducting portions 304.

Analysing which contacts are associated with a code value of "1" and which are associated with a code value of "0", the processor 202 can determine the unique seven bit binary code associated with the absolute rotational position of the rotatable sleeve 406. The processor 202 can then use the seven bit binary code to determine the dialled drug dose. This may be achieved by the processor 202 upon searching a lookup table stored in the ROM 204, the lookup table providing a conversion from the seven bit binary code result to a dose unit dialled.

In addition to (or instead of) determining a dialled dose, the device 100 may be configured to determine an amount of dose that has been dispensed. For example, when an amount of dose has been dispensed the processor 202 may determine the position of the rotatable sleeve 406 relative to the housing 102 in the foregoing manner. In particular the processor 202 may determine the seven bit binary code associated with the absolute rotational position of the rotatable sleeve 406. The dose amount associated with such a binary code may then be determined from a lookup table. The processor 202 may determine the drug dose which has been dispensed (or is yet to be dispensed, if any) by subtracting a remaining drug dose from an initially dialled drug dose. The display 210 may be used to show the dose amount yet to be dispensed if a user does not dispense the full amount of a dialled dose.

Having determined the drug dose which has been dispensed, the processor 202 may store the result in the Flash memory 205. As mentioned above the display 210 may be controlled to display the result of the dispensed dose determination. The display 210 may show the result of the dispensed dose determination for a predetermined time, for example 60 seconds. Alternatively or in addition, the dispensed dose history may be retrieved electronically from the Flash memory 205 by a user of the device 100 or by a health care professional. During dialling of the device, the dialled dose may be indicated to the user in any conventional way, for example by use of numerals printed on the encoded member. In some other embodiments, the dialled dose is not determined or indicated to the user.

Although a seven bit coding system has been described, the third embodiment is equally applicable for any number of contacts greater than three. The seven bit system is preferred as it allows the full 0-80 unit dose range to be absolutely encoded.

Furthermore, the processor 202 may implement the process of checking the contacts 212 while the rotatable sleeve 406 is actually rotating, i.e. while the device 100 is actually being dialled or is being used to dispense a substance. Alternatively the checking process may only be performed when the processor 202 detects that the rotatable sleeve 406 has been in a certain position for a predetermined amount of time (for example 100 milliseconds), thereby indicating that the device 100 has been dialled or dispensed an intended amount by a user.

It will be appreciated that in other arrangements the code defined by the helical track 300 may have a different configuration, in particular it may define a different combination of "0"s and "1"s to that used in the above illustrative example.

Part of an alternative code for the helical track 300 is illustrated in FIG. 26. In this example, the contacts 212 are configured to read every third bit of the code of the helical track 300. At a first position, shown leftmost in FIG. 26, the contacts are coupled to the first, fourth, seventh, etc bit. In the first position, the code seen by the encoder 212 is 1010100. After incrementing by one position, as shown in the middle column of FIG. 26, the contacts 212 connect with the second, fifth, eighth, etc bits of the code of the helical track 300. In the second position, the code is 0010001. In the third position, shown rightmost in FIG. 26, the contacts 212 are connected to the third, sixth, ninth, etc bits of the code formed by the helical track 300. In the third position, the code seen by the encoder 202 is 0000101.

Alternatively, a single-track Gray code equivalent could be used. However, such a code would be relatively long, compared to the codes described above.

In these embodiments, the helical track 300 and also the thread feature 432 of the rotatable sleeve 406 are also both relatively long, because the seven contacts 212 are relatively widely spaced apart along the code formed by the helical track 300.

Some variations of and modification to the third embodiment will now be discussed.

Instead of including the connecting track 300 of the helical track on the engaging face 710 of the thread feature 432 of the rotatable sleeve 406, it may be otherwise provided. For instance, it may be provided on the major inner face of the rotatable sleeve 406, at the part that is closest to the engaging face 710 of the thread feature 432 for example. It may alternatively be provided on the uppermost face 714 of the thread feature 432, in which case connecting tracks may extend around the side face 712 to connect the conductive segments 302 on the engaging face 710 with the connecting track 306 on the bottom face 714. It may alternatively be provided on the side face 712.

The thread features 432 and 436 need not be single start threads. They may alternatively be twin start threads, or triple or higher order start threads.

Instead of the relatively long thread feature being provided on the rotatable sleeve 406, it may instead be provided on the outermost surface of the inner housing 408, and with the previous embodiments. In this case, the rotatable sleeve 406 is provided with a thread feature on its outermost surface. However, this need not be continuous, and may be relatively short or may be a number of short sections of partial thread.

Also, although it is the rotatable sleeve 406 that rotates and the inner housing 408 is fixed relative to the main body 102, it may instead be the inner housing 408 that rotates and the sleeve 406 may be fixed relative to the housing 102.

The processor 202 is capable of determining the extent of rotation of the rotatable sleeve 406 (and thus how far it has travelled axially) by analysing which contacts 212*a*-212*g* engage conductive segments 302 and which contacts engage non-conductive segments 304.

In all of the above embodiments, the helical tracks 300, 300*a*, 300*b*, 301*a*, 301*b* may be formed by wrapping a metallic strip around the inner housing 408 or the rotatable sleeve 406, as the case may be. Such a metallic strip may have a non-conductive backing to support the metallic layer. The non-conductive backing may have an adhesive on the reverse side for securing the strip to the outer surface 440 of the rotatable sleeve 406 or the inner housing 408. The helical tracks 300, 300a, 300b, 301a, 301b may alternatively comprise conductive ink printed onto a non-conductive substrate. This non-conductive substrate may be the inner housing 408 or rotatable sleeve 406 itself or a secondary substrate which is subsequently attached to the inner housing 408 or rotatable sleeve 406. The helical tracks 300, 300a, 300b, 301a, 301b may be formed by wrapping a metallic strip around the inner housing 408 or the rotatable sleeve 406, as the case may alternatively be provided by application of a selective plating technique.

In all of the embodiments, having determined the drug dose which has been dispensed, the processor 202 may store the result in the Flash memory 205. As mentioned above the display 210 may be controlled to display the result of the dispensed dose determination. The display 210 may display the result of the dispensed dose determination for a predetermined time, for example 60 seconds. Alternatively or in addition, the dispensed dose history may be retrieved electronically from the Flash memory 205 by a user of the device 100 or by a health care professional. During dialling of the device, the dialled dose may be indicated to the user in any conventional way, for example by use of numerals printed on the encoded member. In some other embodiments, the dialled dose is not determined or indicated to the user.

Sensing of the presence or absence of track is performed using a contact and the processor. At a general level, this may involve hardware that compares a voltage signal provided by the contact with a threshold and indicting the presence or absence of track through an output that indicates whether the voltage exceeded or did not exceed respectively the threshold. In a processor implementation, it may involve buffering the signal provided by the contact, for instance using an inverter gate or other buffer, sampling the buffered signal and comparing the sampled signal to a reference. Other ways of sensing the presence or absence of track will be apparent to the skilled person.

Finally, it will be appreciated that the above described embodiments are purely illustrative and are not limiting on the scope of the invention. Other variations and modifications will be apparent to persons skilled in the art upon reading the present application. Moreover, the disclosure of the present application should be understood to include any novel features or any novel combination of features either explicitly or implicitly disclosed herein or any generalization thereof and during the prosecution of the present application or of any application derived there from, new claims may be formulated to cover any such features and/or combination of such features.

The invention claimed is:

1. A drug delivery device comprising:
a body component located concentrically within a sleeve, wherein the body component comprises body component thread features and the sleeve comprises sleeve thread features that engage with the body component thread features such that the body component is caused to rotate within the sleeve as the body component and the sleeve component move axially with respect to one another by force of an engaging face of the sleeve thread features against an engaging face of the body component thread features causing sliding of the engaging face of the sleeve thread features over the engaging face of the body component thread features, wherein the body component is an inner housing,
wherein one of the body component and the sleeve constitutes a first part and the other of the body component and the sleeve constitutes a second part, and
wherein a conductive track pattern is formed on the thread features of the first part and plural electrical contacts are formed on the second part such as to contact the conductive track pattern as the body component rotates within the sleeve.

2. The drug delivery device as claimed in claim 1, wherein the conductive track pattern comprises:
a continuous portion that extends helically on the first part and that is not in direct contact with the plural electrical contacts formed on the second part as the body component rotates within the sleeve, and
a discontinuous portion that extends helically on the first part, that is connected to the continuous portion of the conductive track pattern and that is in direct contact with the plural electrical contacts formed on the second part as the body component rotates within the sleeve.

3. The drug delivery device as claimed in claim 2, wherein the discontinuous portion of the conductive track pattern is provided on the engaging face of the thread component of the first part and wherein the continuous portion of the conductive track pattern is provided on a non-engaging face of the thread component of the first part.

4. The drug delivery device as claimed in claim 1, wherein first and second conductive track patterns are formed on the thread features of the first part, and
wherein the plural electrical contacts are formed on the second part such as to contact the first and second conductive track patterns as the body component rotates within the sleeve.

5. The drug delivery device as claimed in claim 1, wherein the conductive track pattern consists of a single conductive track pattern.

6. The drug delivery device as claimed in claim 1, wherein the sleeve thread features form parts of first and second ones of different start threads and wherein the sleeve thread features and the body component thread features form parts of first and second ones of different start threads.

7. The drug delivery device as claimed in claim 1, wherein the thread features of each thread of the first part includes a conductive track pattern and wherein the thread features of each thread of the second part includes respective plural electrical contacts.

8. The drug delivery device as claimed in claim 1, wherein the body component constitutes the first part and wherein the sleeve constitutes the second part.

9. The drug delivery device as claimed in claim 1, wherein the sleeve constitutes the first part and wherein the body component constitutes the second part.

10. The drug delivery device as claimed in claim 1, wherein each of the plural electrical contacts is sprung, thereby to provide a preload force between the sleeve thread features and the body component thread features.

11. The drug delivery device as claimed in claim 1, further comprising a processor configured to receive and interpret electrical signals from each of the plural electrical contacts to determine the position of the cylindrical member relative to the housing.

12. The drug delivery device as claimed in claim 11, further comprising a display in communication with the processor, wherein the processor is configured to cause the display to display information determined by the processor based on the electrical signals.

13. The drug delivery device as claimed in claim 1, wherein the plural contacts are spring biased in a direction towards the conductive track pattern.

14. The drug delivery device as claimed in claim 1, further comprising an outer housing,
    wherein the sleeve and the inner housing are in the outer housing.

15. The drug delivery device as claimed in claim 2, wherein the discontinuous portion comprises a plurality of conductive segments and a plurality of non-conductive segments, and
    wherein the plurality of conductive segments and the plurality of non-conductive segments are arranged in an alternating pattern such that successive ones of the plurality of conductive segments are separated by a respective one of the non-conductive segments.

16. The drug delivery device as claimed in claim 2, wherein the continuous portion couples the discontinuous portion to a battery.

17. The drug delivery device as claimed in claim 1, wherein the engaging face of the body component and the engaging face of the sleeve are transverse to a longitudinal axis of the body component and the sleeve.

18. The drug delivery device as claimed in claim 1, wherein the body component is a hollow cylinder.

19. The drug delivery device as claimed in claim 18, further comprising a spindle arranged in the hollow cylinder of the body component.

20. The drug delivery device as claimed in claim 1, wherein the body component comprises a plastic material,
    wherein, when the body component is the first part, the conductive track pattern is on an exterior surface of the plastic material, and
    wherein, when the body component is the second part, the plural contacts are on the exterior surface of the plastic material.

\* \* \* \* \*